US012721690B1

(12) United States Patent
Rosa

(10) Patent No.: US 12,721,690 B1
(45) Date of Patent: Sep. 1, 2026

(54) ROBOTIC SURGICAL INSTRUMENT HAVING FLUIDICALLY SEALED DRIVE MECHANISM, AND SYSTEMS AND METHODS THEREOF

(71) Applicant: Distalmotion SA, Epalinges (CH)

(72) Inventor: Benoit Della Rosa, Epalinges (CH)

(73) Assignee: Distalmotion SA, Epalinges (CH)

( * ) Notice: Subject to any disclaimer, the term of this patent is extended or adjusted under 35 U.S.C. 154(b) by 0 days.

(21) Appl. No.: 19/346,365

(22) Filed: Sep. 30, 2025

(51) Int. Cl.

| | |
|---|---|
| ***A61B 34/30*** | (2016.01) |
| ***A61B 34/00*** | (2016.01) |
| *A61B 17/29* | (2006.01) |
| *A61B 17/34* | (2006.01) |
| *A61B 34/37* | (2016.01) |

(52) U.S. Cl.
CPC .............. *A61B 34/70* (2016.02); *A61B 34/30* (2016.02); *A61B 2017/2948* (2013.01); *A61B 2017/3419* (2013.01); *A61B 34/37* (2016.02)

(58) Field of Classification Search
None
See application file for complete search history.

(56) References Cited

U.S. PATENT DOCUMENTS

| | | | | |
|---|---|---|---|---|
| 8,939,963 | B2 | 1/2015 | Rogers et al. | |
| 10,413,374 | B2 | 9/2019 | Chassot et al. | |
| 10,646,294 | B2 | 5/2020 | Beira | |
| 10,806,538 | B2 | 10/2020 | Farritor et al. | |
| 11,058,503 | B2 | 7/2021 | Chassot et al. | |
| 12,295,688 | B2 | 5/2025 | Chassot et al. | |
| 2009/0216248 | A1* | 8/2009 | Uenohara | A61B 34/70 606/130 |
| 2014/0005661 | A1 | 1/2014 | Shelton, IV et al. | |
| 2019/0274781 | A1 | 9/2019 | Lambrecht et al. | |
| 2020/0405403 | A1 | 12/2020 | Shelton, IV et al. | |

(Continued)

FOREIGN PATENT DOCUMENTS

| | | | |
|---|---|---|---|
| WO | WO-2015175200 A1 * | 11/2015 | A61B 46/10 |
| WO | WO-2016183054 A1 * | 11/2016 | A61B 34/35 |

(Continued)

OTHER PUBLICATIONS

U.S. Appl. No. 19/286,070, Non-Final Office Action mailed Oct. 2, 2025; Inventor Crozier, James et al.; 30 pages.

(Continued)

*Primary Examiner* — James Kish
(74) *Attorney, Agent, or Firm* — Cooley LLP

(57) ABSTRACT

Devices, systems, and methods herein relate to surgical robotic systems, for example, a surgical instrument removably coupled to a robotic arm. Devices may include a shaft including a proximal end and a distal end. The shaft may define a lumen extending between the proximal end and the distal end. An end effector may be disposed at the distal end of the shaft. A proximal head may be disposed at the proximal end of the shaft. The proximal head may include at least one housing defining a plurality of slots and a plurality of engagement elements. Each engagement element may be disposed in a separate slot of the plurality of slots. Each engagement element of the plurality of engagement elements may have a first end that is coupled to the end effector via a transmission member and a second end that is configured to be coupled to a drive unit.

19 Claims, 15 Drawing Sheets

(56) References Cited

U.S. PATENT DOCUMENTS

| | | | |
|---|---|---|---|
| 2021/0315660 | A1 | 10/2021 | Williams et al. |
| 2022/0079696 | A1 | 3/2022 | Nichols et al. |
| 2022/0080602 | A1 | 3/2022 | Nobles et al. |
| 2022/0202438 | A1 | 6/2022 | Hibner et al. |
| 2024/0006048 | A1 | 1/2024 | Shelton, IV et al. |

FOREIGN PATENT DOCUMENTS

| | | | | | |
|---|---|---|---|---|---|
| WO | WO-2017015599 | A1 * | 1/2017 | ............. | A61B 34/37 |
| WO | WO-2018207136 | A1 * | 11/2018 | ............. | A61B 90/94 |
| WO | WO-2019155383 | A1 | 8/2019 | | |
| WO | WO-2020141487 | A2 | 7/2020 | | |
| WO | WO-2024084422 | A1 | 4/2024 | | |

OTHER PUBLICATIONS

U.S. Appl. No. 19/286,070, filed Jul. 30, 2025; Inventor Crozier, James et al.

U.S. Appl. No. 19/346,327, filed Sep. 30, 2025; Inventor Nicolet, Romain et al.

U.S. Appl. No. 19/402,449, filed Nov. 26, 2025; Inventor Crozier, James.

U.S. Appl. No. 19/431,629, filed Dec. 23, 2025; Inventor Rozand, Guillaume et al.

* cited by examiner 7C
7C
640
624

624
624

740
9B
9C

ROBOTIC SURGICAL INSTRUMENT HAVING FLUIDICALLY SEALED DRIVE MECHANISM, AND SYSTEMS AND METHODS THEREOF

TECHNICAL FIELD

The devices, systems, and methods herein relate to surgical robotic systems, for example, a surgical instrument removably couplable to a robotic arm.

BACKGROUND

Traditional surgical robotic systems may include a robotic device including a robotic arm coupled to a surgical instrument through a sterile interface. The robotic arm may include a hub configured to drive the surgical instrument. The sterile interface allows the transmission of force and movements from the hub to the surgical instrument while providing a sterile barrier. During a surgical procedure, some conventional surgical instruments may be susceptible to liquid ingress. For example, a distal end of the instrument may be advanced into a patient's body such that bodily fluids including blood may enter a shaft of the instrument. However, if the fluid within the instrument flows towards the hub (e.g., due to gravity) and exits at a proximal portion of the instrument, then the electronic components of the hub that come into contact with the fluid may become damaged. As such, additional devices, systems, and methods for a surgical instrument are desirable.

SUMMARY

Devices, systems, and methods herein relate to a surgical instrument providing improved liquid management (e.g., liquid tightness) that may reduce damage (e.g., contamination) to the surgical robotic system and fluid contact with a sterile interface. In some embodiments, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include at least one housing defining a plurality of slots and a plurality of engagement elements. Each engagement element of the plurality of engagement elements may be disposed in a separate slot of the plurality of slots. Each engagement element of the plurality of engagement elements may have a first end that is coupled to the end effector via a transmission member and a second end that is configured to be coupled to a drive unit of a surgical robotic system such that actuation of the engagement element by the drive unit is configured to drive movement of the end effector in at least one degree-of-freedom. A sealing unit may be configured to seal a space between the at least one housing and the plurality of engagement elements.

In some embodiments, the at least one housing includes a proximal housing and a distal housing. The proximal and distal housings may collectively define a plurality of passages within which the plurality of engagement elements translate. In some embodiments, the sealing unit may be disposed between the proximal housing and the distal housing and may be configured to seal spaces between each engagement element of the plurality of engagement elements and neighboring portions of the proximal and distal housings. In some embodiments, the sealing unit may include a plurality of seals. Each seal of the plurality of seals may be configured to be disposed around a respective engagement element of the plurality of engagement elements and to seal the spaces between the engagement element and the neighboring portions of the proximal and distal housings. In some embodiments, each engagement element of the plurality of engagement elements may be configured to be actuated by the drive unit to axially translate the engagement element while the respective seal of the plurality of seals disposed around the engagement element is held stationary relative to the engagement element by the proximal and distal housings. In some embodiments, each seal of the plurality of seals may include an O-ring. In some embodiments, each seal of the plurality of seals may be disposed on the respective engagement element of the plurality of engagement elements between the first and second ends of the engagement element.

In some embodiments, each engagement element of the plurality of engagement elements may be configured to be actuated by the drive unit to axially translate the engagement element relative to the sealing unit.

In some embodiments, the apparatus may include a knob, the knob configured to be rotated and/or translated relative to the proximal head to lock the apparatus to the surgical robotic system.

In some embodiments, each transmission member may include a distal section comprising a cable and a proximal section comprising a hypotube. The apparatus may further include a seal disposed around the hypotubes of the transmission members and configured to seal spaces between outer surfaces of the hypotubes and an inner surface of the shaft. In some embodiments, the seal may include a plurality of openings that are distributed around a periphery of the seal. In some embodiments, the openings of the plurality of openings may be distributed around the periphery of the seal.

Also described are apparatuses with a plurality of seals. In some embodiments, an apparatus may include a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a plurality of engagement elements. Each engagement element of the plurality of engagement elements may extend from an interior of the apparatus through a passage to an exterior of the apparatus. Each engagement element of the plurality of engagement elements may have a first end disposed in the interior that is coupled to the end effector via a transmission member and a second end disposed on the exterior that is configured to be coupled to a drive unit of a surgical robotic system such that actuation of the engagement element by the drive unit is configured to drive movement of the end effector in at least one degree-of-freedom. The apparatus may include a plurality of seals. Each seal of the plurality of seals may be disposed around a respective engagement element of the plurality of engagement elements at the passage.

In some embodiments, each seal of the plurality of seals may include an O-ring. In some embodiments, each engagement element of the plurality of engagement elements may include a cylindrical elongate portion disposed between the first and second ends. Each O-ring of the plurality of seals may be disposed around the cylindrical elongate portion of the plurality of engagement elements.

In some embodiments, the proximal head may further include a housing that defines a plurality of slots. Each engagement element of the plurality of engagement elements may be disposed within a separate slot of the plurality of slots and be configured to axially translate within the slot in response to the actuation of the engagement element by the drive unit. In some embodiments, the plurality of engagement elements may be disposed around a periphery of the housing.

In some embodiments, each engagement element of the plurality of engagement elements may be configured to be actuated by the drive unit to axially translate the engagement element relative to the plurality of seals. In some embodiments, the proximal head may further include a proximal housing and a distal housing. The proximal and distal housings may collectively define the passages through which the plurality of engagement elements extend. In some embodiments, the proximal and distal housings may include one or more stopping surfaces configured to limit movement of the plurality of seals while the plurality of engagement elements axially translates relative to the plurality of seals.

In some embodiments, each transmission member may include a distal section comprising a cable and a proximal section comprising a hypotube. The apparatus may further comprise a seal disposed around the hypotubes of the transmission members and configured to seal spaces between outer surfaces of the hypotubes and an inner surface of the shaft.

DETAILED DESCRIPTION

Figure 1:
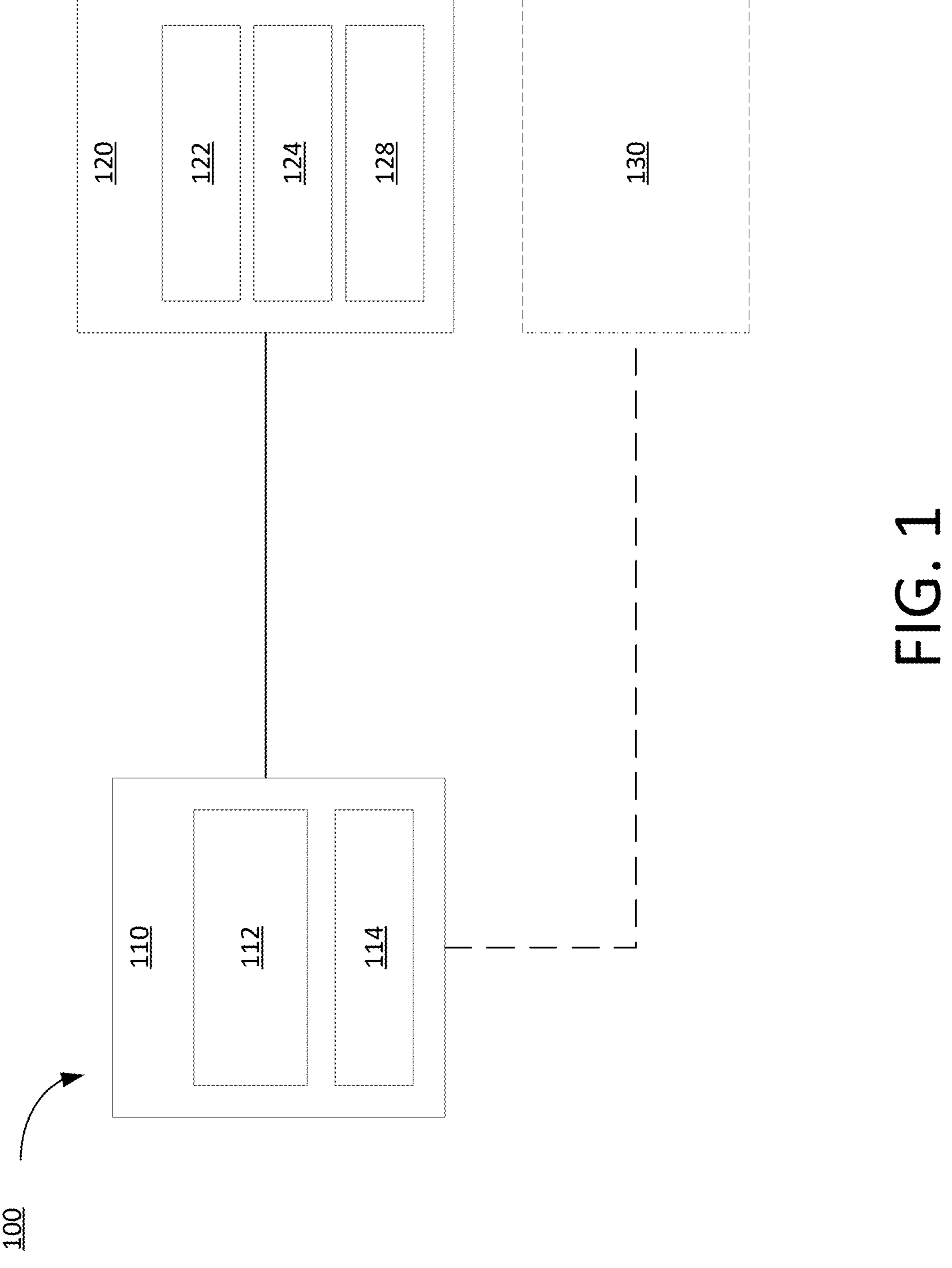
FIG. 1 schematically depicts a surgical robotic system, according to embodiments.

Described here are surgical instruments used in a surgical robotic system. These systems, devices, and methods may include mechanisms to fluidically seal a drive mechanism of a surgical instrument. The systems, devices and methods described herein may, for example: provide a fluid-tight seal at a proximal portion of the instrument, thereby preventing fluid ingress into one or more of a sterile interface and a hub of the instrument; improve performance of a seal coupled to one or more transmission members and a shaft of the instrument; reduce the "pumping effect" of transmission cables and corresponding to fluid ingress; provide a seal geometry that improves sealing performance and lifetime; facilitate assembly of one or more transmission members with a proximal seal of the surgical instrument; facilitate actuation of transmission cables by a driving unit of a surgical robotic system; eliminate a direct path from a lumen of the instrument to an external environment; and retain any liquid within the instrument even when the instrument is angled where the proximal head is lower than the instrument tip.

By contrast, conventional surgical robotic systems manage fluid using one or more of a seal disposed at a distal portion of an instrument and a sterile interface coupled to a robotic arm configured to form a connector with respect to a drive mechanism (e.g., hub) of the surgical instrument. For example, elastomeric seals have been used between an instrument tip and an instrument shaft. The seal (e.g., rubber, silicone) may be disposed at a distal interior portion of the instrument (e.g., behind or on the tip). A set of cables may pass tightly through corresponding holes in the seal to prevent liquid from entering the shaft of the instrument. However, the set of cables may be braided and have a rough surface that causes wear on the distal seal as the cables are translated relative to the seal during use. Due to this friction, the seals will lose performance and allow fluid ingress over time. Furthermore, rubber seals may become less elastic and flexible over time, leading to loss of performance and efficiency. Finally, the translation of the braided cables through the seal may generate a "pumping effect" whereby fluid is directly pumped into the shaft of the instrument by the cables during their operation.

Conventional surgical robotic systems having a sterile interface and sterile drape manage fluid by forming a fluid barrier to protect the robotic arm and drive mechanism. For example, liquid (e.g., blood, saline) flowing from the patient and through the surgical instrument will flow onto the drape, which may create a mess in an operating environment. However, the use of a sterile interface and sterile drape to a surgical robotic system may increase the complexity of the system and procedure. It should be noted that any of the instruments described herein may be used independently of or in combination with conventional solutions (e.g., distal seal, sterile drape).

In some variations, the apparatuses described here may provide an instrument with a seal near a proximal end. For example, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a plurality of engagement elements. The plurality of engagement elements may be configured to be coupled to one or more drive units of a surgical robotic system that are configured to actuate the plurality of engagement elements. A plurality of transmission members may be disposed within the lumen. Each transmission member of the plurality of transmission members may couple a separate engagement element of the plurality of engagement elements to the end effector such that the actuation of the plurality of engagement elements causes movement of the end effector in at least one degree-of-freedom. A seal may be disposed around the plurality of transmission members and within the shaft near the proximal end of the shaft. The seal may be configured to form a fluid-tight seal between the plurality of transmission members and an inner surface of the shaft.

Also described here are apparatuses including a seal disposed around one or more hypotubes. For example, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a plurality of engagement elements. The plurality of engagement elements may be configured to be coupled to one or more drive units of a surgical robotic system that are configured to actuate the plurality of engagement elements. A plurality of transmission members may be disposed within the lumen. Each transmission member of the plurality of transmission members may couple a separate engagement element of the plurality of engagement elements to the end effector such that the actuation of the plurality of engagement elements causes movement of the end effector in at least one degree-of-freedom. Each transmission member of the plurality of transmission members may include a proximal hypotube attached to a distal cable. A seal may be disposed around the proximal hypotube of each transmission member of plurality of transmission members and within the shaft. The seal may be configured to form a fluid-tight seal between the proximal hypotube and an inner surface of the shaft. A hypotube is a tube or rod attached (e.g., crimped or welded) to a cable or wire, extending the cable or wire in its longitudinal direction to transmit mechanical work.

Also described here are apparatuses including a proximal head having sealing. For example, an apparatus may comprise a shaft including a proximal end and a distal end. The shaft may define a lumen extending between the proximal end and the distal end. An end effector may be disposed at the distal end of the shaft. A proximal head may be disposed at the proximal end of the shaft. The proximal head may include at least one housing defining a plurality of slots and a plurality of engagement elements. Each engagement element of the plurality of engagement elements may be disposed in a separate slot of the plurality of slots. Each engagement element of the plurality of engagement elements may have a first end that is coupled to the end effector via a transmission member and a second end that is configured to be coupled to a drive unit of a surgical robotic system such that actuation of the engagement element by the drive unit is configured to drive movement of the end effector in at least one degree-of-freedom. A sealing unit may be configured to seal a space between the at least one housing and the plurality of engagement elements to prevent fluids from exiting an interior space of the apparatus.

Also described here are apparatuses including a plurality of seals. For example, an apparatus may include a shaft including a proximal end and a distal end. The shaft may define a lumen extending between the proximal end and the distal end. An end effector may be disposed at the distal end of the shaft. A proximal head may be disposed at the proximal end of the shaft. The proximal head may include a plurality of engagement elements. Each engagement element of the plurality of engagement elements may extend from an interior of the apparatus through a passage to an exterior of the apparatus. Each engagement element of the plurality of engagement elements may have a first end disposed in the interior that is coupled to the end effector via a transmission member and a second end disposed on the exterior that is configured to be coupled to a drive unit of a surgical robotic system such that actuation of the engagement element by the drive unit is configured to drive movement of the end effector in at least one degree-of-freedom. The apparatus may include a plurality of seals. Each seal of the plurality of seals may be disposed around a respective engagement element of the plurality of engagement elements at the passage to seal an interior of the apparatus from the exterior of the apparatus.

Systems and Devices

FIG. 1 schematically depicts a surgical robotic system 100, according to embodiments. The system 100 can include a master console 110 and one or more slave console(s) 120. Optionally, the system 100 can also include an imaging device 130, such as, for example, an endoscopic camera or other visualization device.

The master console 110 can be operatively coupled to the slave console(s) 120. For example, the master console 110 can be coupled to the slave console(s) 120 via wired and/or wireless connections. The master console 110 can include one or more master manipulator(s) 112 and one or more master controller(s) 114. In some embodiments, the master manipulator(s) 112 can include a plurality of master links that are interconnected by a plurality of joints. Movement can be applied to the master manipulator(s) 112 via a handle, which can be actuated by a user (for instance a sterile user, e.g., a surgeon). The movement of the master manipulator(s) 112 and one or more actuators of the handle can be sensed, e.g., using a plurality of sensors, and transmitted to the master controller(s) 114.

The master console 110 and the slave console(s) 120 can be examples of surgical robotic devices. In operation, the master console 110 can be configured to teleoperate the slave console(s) 120 to perform a surgical procedure. As further described below, movements of the master manipulator(s) 112 can be sensed at the master console 110, which can be translated into movements of portions of the slave console(s) 120.

Each slave console 120 can include a slave manipulator 122 and/or an instrument 128 (e.g., surgical instrument) that is coupled to the slave manipulator 122. The slave manipulator 122 can be implemented as a robotic arm, e.g., including a plurality of links that are interconnected by a plurality of corresponding joints. The slave console(s) 120 can include one or more drive units, actuators, or motors that control movement of the plurality of links and joints of the slave manipulator 122. The instrument 128 can be removably coupled to the slave manipulator 122. When the instrument 128 is coupled to the slave manipulator 122, the slave manipulator 122 can be configured to support the instrument 128 and to control its movements. In particular, the slave manipulator 122 can be configured to control and move the instrument 128 in a plurality of degrees of freedom (DOF), including translational and/or rotational movement. The slave manipulator 122 can be configured to control the movements of the instrument 128 in a manner responsive to movements applied at the handle of the master console 110. In particular, the master console 110 can generate instructions or commands based on movements applied at the handle and transmit those instructions or commands to the slave console(s) 120 to cause movement of the slave manipulator 122 and/or the instrument 128. The slave console(s) 120 can include a slave controller 124 that can be configured to interpret the instructions or other signals from the master console 110 and to control the movement of the slave manipulator 122 and/or the instrument 128.

While the slave console 120 is described as having a slave manipulator 122 and an instrument 128, it can be appreciated that a single slave console 120 can include more than one slave manipulator 122 and/or more than one instrument 128. For example, a slave console 120 can include two slave manipulators 122 that each support one or more instruments 128.

The master controller(s) 114 and the slave controller(s) 124, as described herein, can include one or more of a memory, a processor, a communications interface, and/or an input/output device. The memory can include any type of suitable non-transitory computer readable media that can store instructions that can be executed by one or more processors. The memory can be, for example, a random access memory (RAM), a memory buffer, a hard drive, a database, an erasable programmable read-only memory (EPROM), an electrically erasable read-only memory (EEPROM), a read-only memory (ROM), and/or so forth. The processor can be any suitable processing device configured to run and/or execute functions associated with the surgical robotic system 100. The processor can be a general purpose processor, a Field Programmable Gate Array (FPGA), an Application Specific Integrated Circuit (ASIC), a Digital Signal Processor (DSP), and/or the like. The communications interface can include wired and/or wireless interfaces for receiving information and/or sending information to other devices. The input/output device can include one or more displays, audio devices, touchscreens, keyboards, or other input or output devices for presenting information to and/or receiving information from a user.

Further examples of surgical robotic systems and instruments are described in PCT Patent Application No. PCT/IB2020/050039, filed Jan. 4, 2020, titled "Surgical Robot Systems Comprising Robotic Telemanipulators and Integrated Laparoscopy"; PCT Patent Application No. PCT/IB2019/050961, filed Feb. 6, 2019, titled "Surgical Robot Systems Comprising Robotic Telemanipulators and Integrated Laparoscopy"; PCT Patent Application No. PCT/IB2023/060543, filed Oct. 19, 2023, titled "Pivot Joints for Surgical Cutting Devices, and Systems Thereof"; and U.S. patent application Ser. No. 19/286,070, filed Jul. 30, 2025, titled "Systems, Devices, and Methods for Sealing and Venting a Surgical Instrument of a Surgical Robotic System." The disclosures of each of the foregoing applications are incorporated by reference herein.

Figure 2:
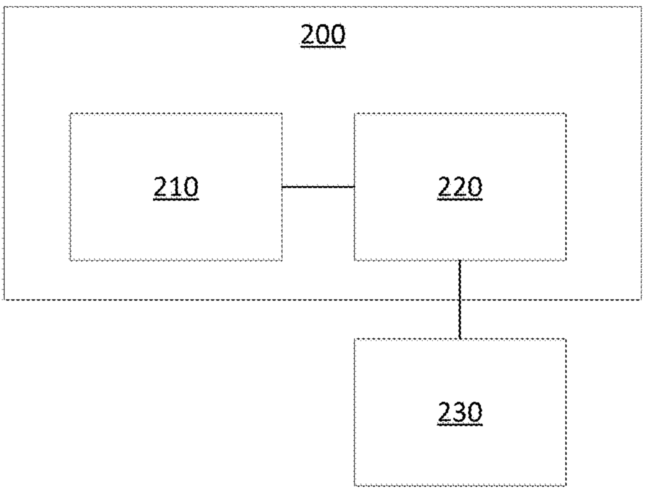
FIG. 2 schematically depicts a manipulator of a surgical robotic system, according to embodiments.

FIG. 2 schematically depicts a slave manipulator 200 of a slave console, according to embodiments. The slave manipulator 200 can include an actuator 210 and an instrument interface 220. The actuator(s) 210 can include one or more electric actuators (e.g., motors), mechanical actuators (e.g., pulleys, chains, gears, shafts, etc.), or other drive mechanisms that are configured to actuate or move one or more components of the slave manipulator 200 and/or other components connected thereto. For example, the actuator(s) 210 can be configured to move the plurality of links and joints of the slave manipulator 200, the instrument interface 220, and/or one or more component(s) of the instrument 230. The instrument 230 can be coupled to the actuator 210 via the instrument interface 220. In some embodiments, the instrument interface 220 can include a hub for receiving the instrument 230. The hub can be mounted on the distal end of the slave manipulator 200, and define an opening for receiving the instrument 230. In some embodiments, the instrument interface 220 can include or be coupled to a sterile adapter or shield. The sterile adapter can be configured to be received within the hub, and can define a lumen for receiving a sterile instrument 330. Suitable examples of instrument hubs and sterile shields are described with reference to PCT Patent Application No. PCT/IB2018/053272, filed May 11, 2018, titled "Translational instrument interface for surgical robot and surgical robot systems comprising the same," and incorporated herein by reference. The instrument 230, when coupled to the instrument interface 220, can be moved by one or more actuator(s) 210, e.g., in one or more degrees of freedom. In some embodiments, the instrument interface 220 may be configured to receive more than one instrument 230.

Figure 3:
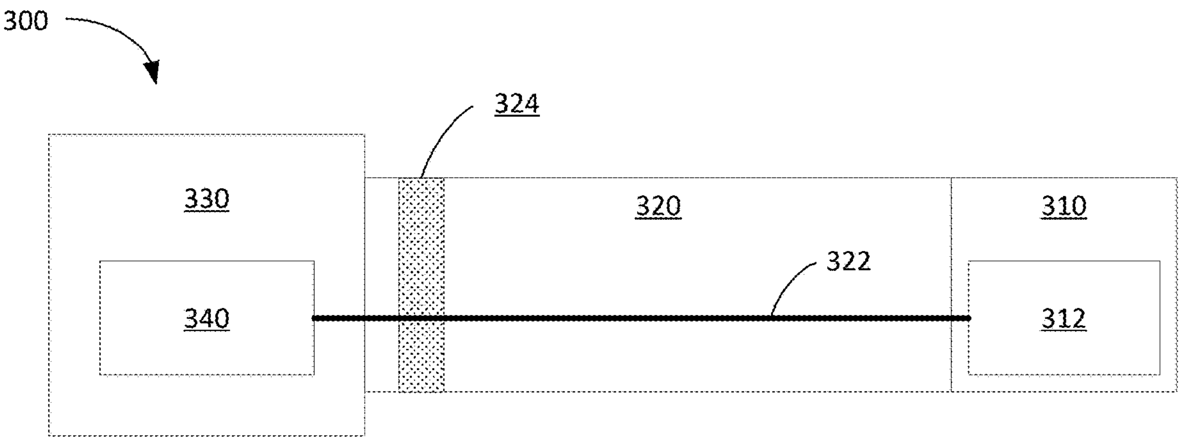
FIG. 3 schematically depicts the instrument of the surgical robotic system of FIG. 2, according to embodiments.

FIG. 3 schematically depicts an instrument 300 (e.g., a surgical instrument of a surgical robotic system, such as, for example, surgical robotic system 100), according to embodiments. The instrument 300 can include a proximal head 330, a shaft 320, and a distal end effector 310. The proximal head 330 can be configured to couple to the instrument interface (e.g., instrument interface 220, as shown in FIG. 2). The proximal head 330 can include one or more engagement elements or engagement elements 340 (e.g., engagers). The engagement elements 340 can be coupled to one or more transmission members 322 (e.g., force transmitting elements such as cables, wires, pulleys, rods, etc., or electrical transmitting elements such as wires, leads, electrodes, etc.) disposed in the shaft 320 of instrument 300. The shaft 320 can be an elongate structure, e.g., an elongate cylinder. The shaft 320 can define a lumen (or plurality of lumens) for housing the transmission member 322.

In some embodiments, the shaft 320 may include one or more seals 324 (e.g., proximal seal) disposed within a shaft 320 (e.g., proximal portion of shaft 320) and configured to reduce (e.g., prevent) liquid ingress from the shaft 320 to the proximal head 330. For example, the seals 324 may be configured to prevent a fluid pathway from an interior of the instrument 300 to an exterior environment (e.g., sterile drape and manipulator 200 (e.g., actuator 210, instrument interface 220)). In embodiments, the engagement elements 340 include one or more extensions, protrusions, latches, tabs, hooks, ports, electrical contacts, or other suitable structure that can be configured to engage with corresponding structure of the instrument interface 220. In an embodiment, the engagement elements 340 can include radially extending tabs (e.g., engagement portions) that are configured to be received in receptacles disposed in a hub of the slave manipulator 200. The receptacles can be driven by the actuator(s) 210 to move, to thereby transmit forces to the engagement elements 340. Examples of suitable engagement elements (or engagers) and receptacles are described in PCT Patent Application No. PCT/IB2018/053272, incorporated above by reference. While engagement elements and receptacles are described with reference to FIG. 2, it can be appreciated that any suitable form of coupling that allows the actuator(s) 210 of the slave manipulator to couple to one or more actuated elements 312 of the end effector 310 to thereby actuate the actuated elements 312 in one or more degrees of freedom can be used. For example, in some embodiments, the coupling between the instrument interface 220 and the instrument 300 can include a mechanical coupling (e.g., latches, pin and hole, grippers, fasteners, etc.), a magnetic coupling (e.g., electromagnets, permanent magnets, etc.), and/or an electrical coupling.

The end effector 310 can be a surgical tool, such as, for example, a set of jaws, a clamp, a grasper (e.g., bipolar Johann grasper, bipolar Maryland dissector, needle holder), a blade, a scissor, a hook, a needle, a stapler, an electrocautery device, an endoscope, and the like. The end effector 310 can include one or more actuated elements 312, e.g., one, two, three, four, five, six, seven, eight, or more actuated elements. The actuated elements 312 can be configured to be actuated (e.g., driven to move or otherwise operate) by the actuator(s) 210 via the engagement element 340 and the transmission elements 322. For example, the actuated elements 312 can include jaws, clamps, or cutting elements that can be actuated in one or more degrees of freedom, e.g., open/close, pitch, yaw, translation, etc.

In an embodiment, the end effector 310 can be a surgical scissor that includes a pair of jaws or cutting members. Accordingly, the one or more actuated elements 312 may move (e.g., rotate, pivot, translate) in one or more degrees of freedom. In embodiments with a plurality of actuated elements (e.g., two actuated elements), the movement of the actuated elements relative to each other may facilitate opening and/or closing the end effector 310. For example, a first actuated element may be moved (e.g., rotated) in a direction towards a second actuated element, such that cutting portions of the actuated elements may come into contact. According to some embodiments, each of the actuated elements can move toward or away from each other. In yet further embodiments, each of the actuated elements may be moved together in the same direction, such that the actuated elements may maintain an opening angle defined therebetween. The direction and magnitude of movement of the end effector 310 can be controlled via forces applied to the engagement elements 340 by one or more actuator(s) 210. The movement of the end effector 310 can provide adjustability and flexibility to the user while performing a cutting process. Further details of surgical tools with two actuating members are described in PCT Patent Application No. PCT/IB2023/060543, incorporated above by reference.

Figure 4:
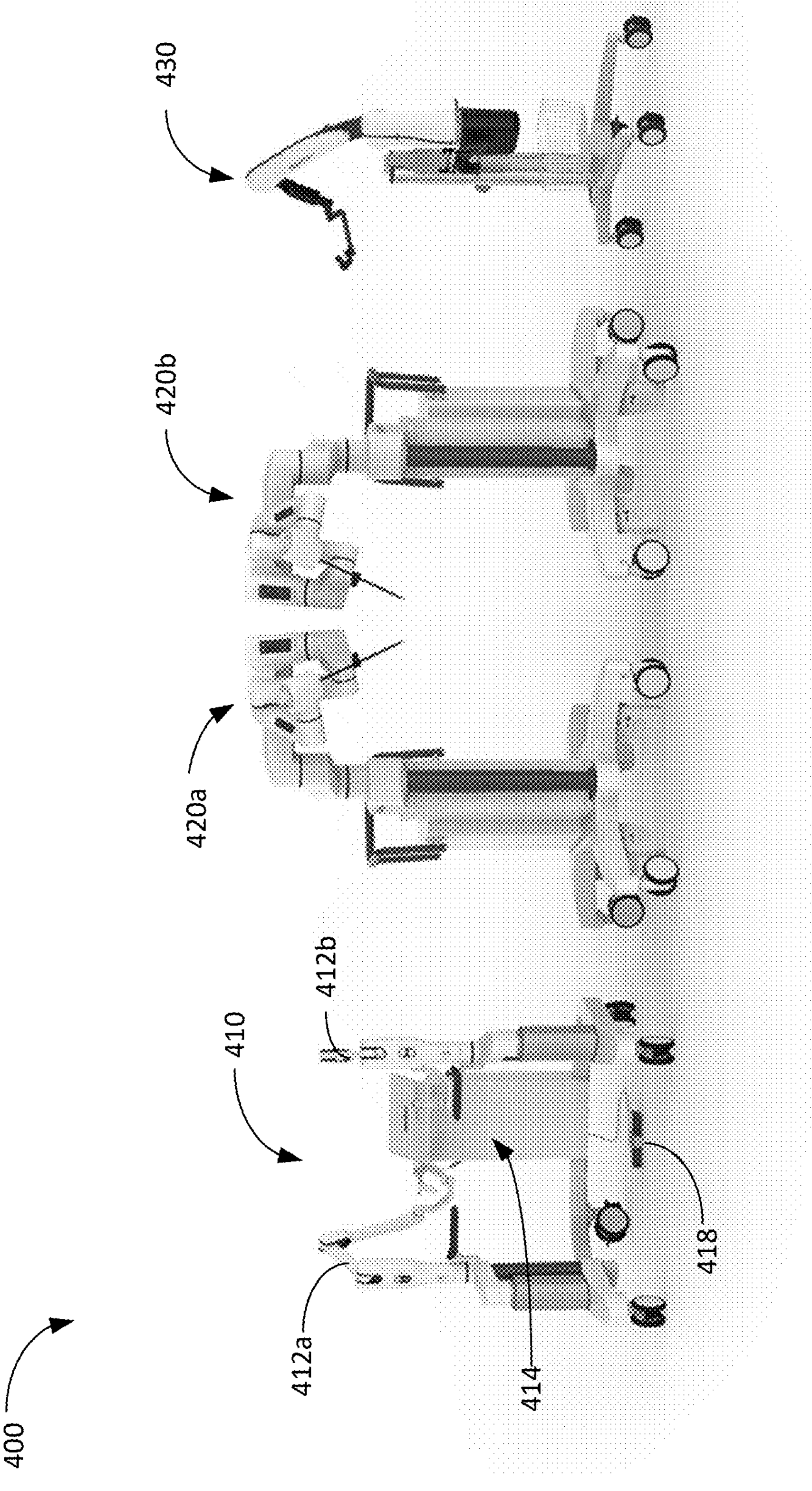
FIG. 4 shows an example surgical robotic system including a master console and multiple slave manipulators, according to embodiments.

FIG. 4 depicts an example of a surgical robotic system 400, according to embodiments. The surgical robotic system 400 can be structurally and/or functionally similar to other surgical robotic systems described herein, including, for example, the surgical robotic system 100, and therefore can include components that are structurally and/or functionally similar to the components of such other systems. For example, the surgical robotic system 400 can include a master console 410 including two master manipulators 412*a* and 412*b* (e.g., left and right manipulators) and a master controller 414, two slave consoles 420*a*, 420*b* (e.g., left and right slave consoles), and an imaging device implemented as an endoscope device 430.

In operation, movement of the first slave manipulator 412*a* (and handle coupled thereto) can be sensed and transmitted to the master controller 414, which can then send instructions to a first slave console 420*a* to control the movement of the first slave console 420*a*. Similarly, movement of the second slave manipulator 412*b* (and handle coupled thereto) can be sensed and transmitted to the master controller 414, which can then send instructions to a second slave console 420*b* to control the movement of the second slave console 420*b*. In some embodiments, the master console 410 can also include one or more foot pedal(s) or other actuator(s), which can be depressed to engage or release a clutch. When the clutch is engaged (e.g., by depressing one or more foot pedal(s)), the master controller 414 can be configured to send instructions that cause the slave consoles 420*a*, 420*b* to replicate movements of the master manipulators 412*a*, 412*b*. And when the clutch is not engaged, the master controller 414 may pause sending instruction to the slave consoles 420*a*, 420*b*, such that the slave consoles 420*a*, 420*b* do not replicate the movements of the master manipulators 412*a*, 412*b* and/or deactivate the movement of the slave console(s) 420*a*, 420*b* in some other manner.

Figure 5:
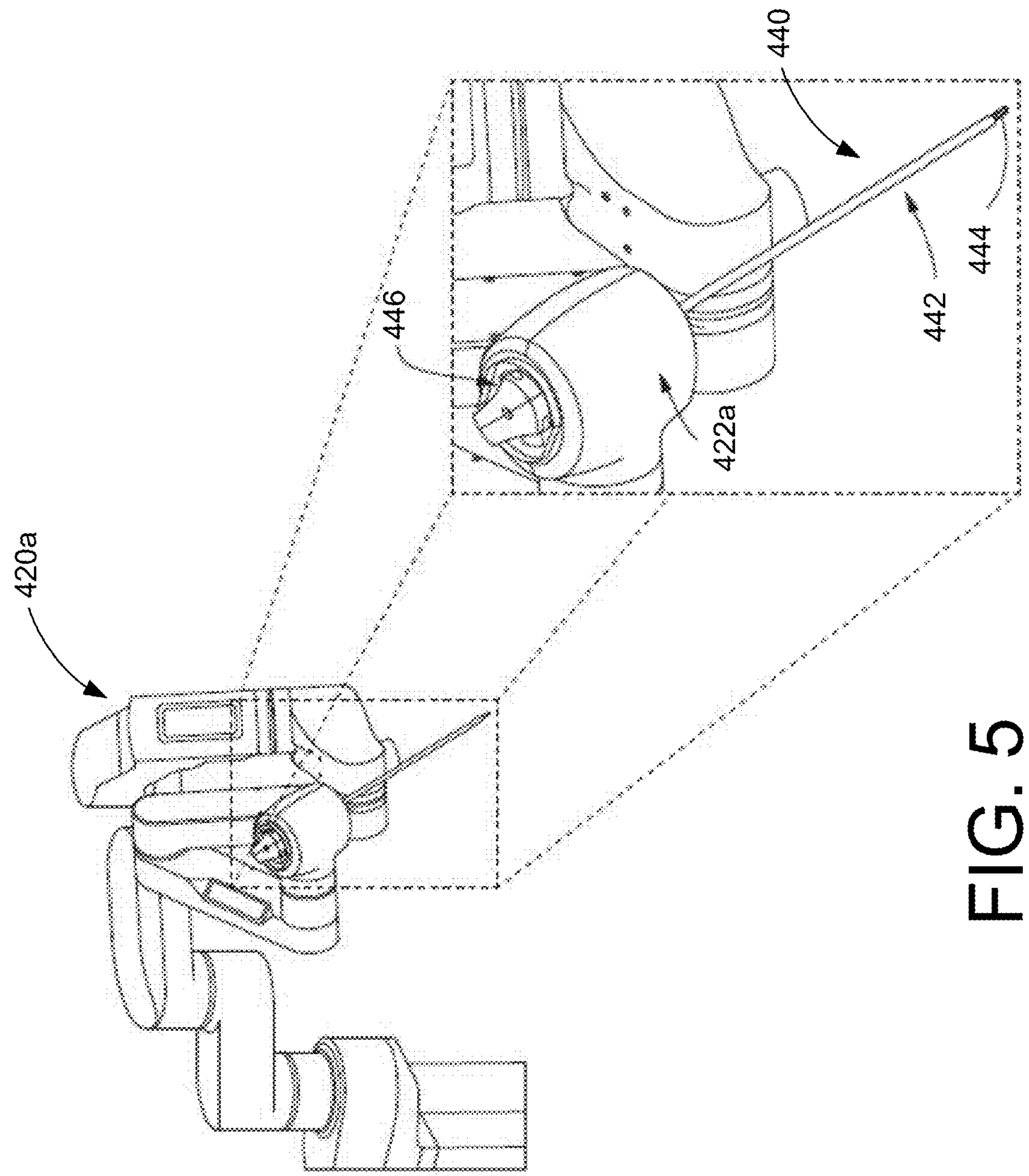
FIG. 5 depicts a detailed view of an instrument coupling of a surgical robotic system, according to embodiments.

FIG. 5 provides a close-up view of an instrument 440 positioned in a hub of a slave manipulator of a slave console 420*a*, according to embodiments. As shown in FIG. 5, the instrument 440 has a proximal head 446, a shaft 442, and a distal end effector 444. The instrument 440 can be structurally and/or functionally similar to other instruments described herein, including for example, instrument 128, 230, 330, 600, 800, 900. The proximal head 446 of the instrument 440 can be releasably coupled to a hub or instrument interface 422*a* of the slave manipulator. The hub 422*a* can define an opening through which the instrument 440 can be inserted. The instrument 440, after being inserted into the hub 422*a* and coupled to the slave manipulator, can be configured to be actuated in one or more degrees of freedom, as described above.

Figure 6:
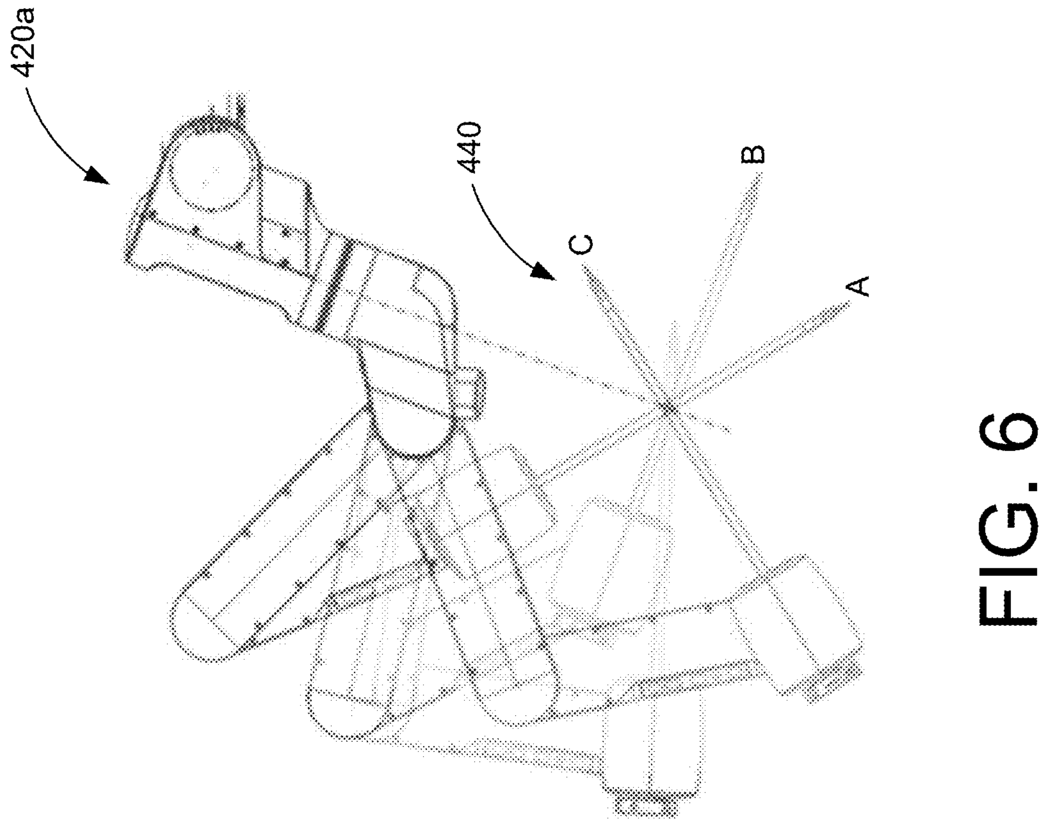
FIG. 6 depicts a detailed view of an instrument coupled to a surgical robotic system in a plurality of configurations, according to embodiments.

FIG. 6 depicts a detailed view of an instrument 440 coupled to a slave manipulator of a slave console 420*a* of surgical robotic system in a plurality of configurations. For example, the instrument 440 may be repositioned to any one of orientations A, B, and C by the slave manipulator while maintaining a predetermined remote center-of-motion. While in orientations A and B, the hub 422*a* and a proximal end of the instrument 440 is higher than a distal end of the instrument 440 such that any fluid inside the instrument 440 is biased towards the end effector of the instrument 440 due to gravity. In some orientations, however, the hub 422*a* may be more susceptible to proximal fluid flow through the instrument 440 due to gravity. For example, in orientation C, the hub 422*a* may be lower than a tip of the instrument 440 such that fluid flowing in an interior of the instrument 440 can flow towards a proximal end of the instrument 440 and the hub 422*a*. Without the seal(s) as described herein, such fluid flow can lead to fluid leakage into the hub and other robotic portions of system, which can lead to damage and/or failure of the system.

Surgical Instrument

Figure 7A:
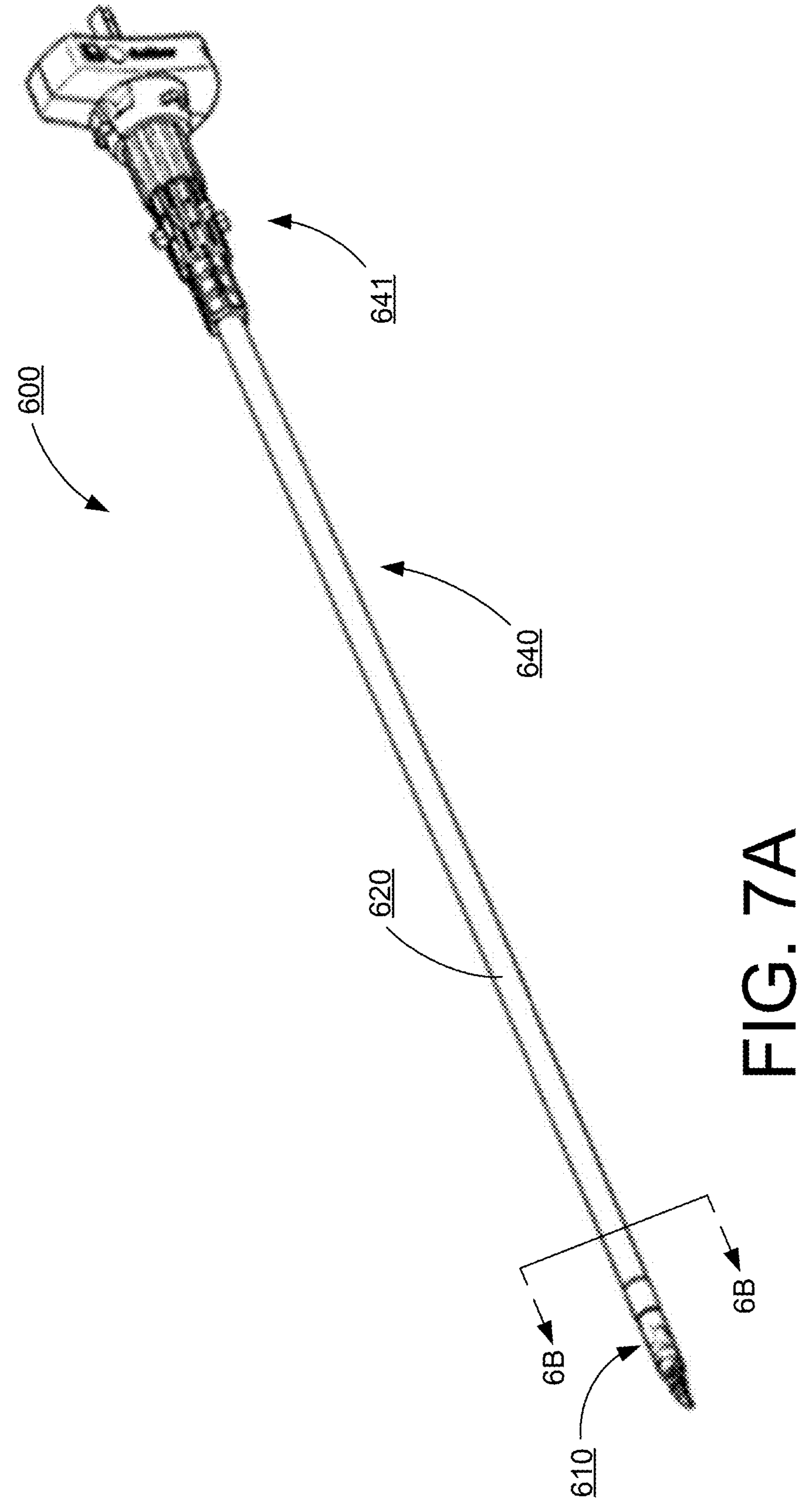
FIG. 7A depicts a surgical instrument of a surgical robotic system, according to embodiments.

Referring now to FIG. 7A, an example surgical instrument 600 is provided. The surgical instrument 600 can be structurally and/or functionally similar to other instruments described herein, including, for example instruments 128, 230, 330, 440, 700, 800, etc. Surgical instrument 600 may include a proximal region including an instrument head or proximal head 641, a distal region having an end effector 610, and an instrument shaft 620 extending between the proximal region and the distal region. In some embodiments, the end effector 610 may be removably coupled to the shaft 620. In some embodiments, the shaft 620 may be removable from the proximal head 640 and/or end effector 610.

As shown in FIG. 7A, the instrument 600 may include one or more transmission members 640 configured to be translated within the shaft 620 to thereby actuate the end effector 610 in one or more degrees of freedom, e.g., pitch, yaw, and open/close. For example, the proximal head 641 may be operatively coupled to the end effector 610 via a plurality of transmission members (e.g., force transmitting elements, cables, hypotubes) extending from the proximal head 641 through the instrument shaft 620 to the end effector 610. In some embodiments, one or more transmission members 640 may be actuated to actuate one or more components of the end effector 610, e.g., in pitch and/or yaw degrees of freedom. The proximal head 641 may be removably engaged with corresponding structures of a hub of a slave console (e.g., slave console 120), e.g., via a releasable hook mechanism, such that movements at a handle of a master console (e.g., operated by a surgeon) may be replicated at end effector 610 of surgical instrument 600.

In some embodiments, an instrument may be configured to couple to a sterile interface using axial translation (e.g., pushing) and rotational movement. The instruments can be reusable instruments, e.g., instruments that are designed to be used in more than one surgical procedure, and can be disinfected or sterilized before each procedure. Alternatively, the instruments can be single-use instruments or disposable instruments, e.g., instruments that are designed to be used in a single procedure and discarded. In both types of instruments, it can be important to sterilize an interior space or internal components of the instrument, as further described below. The interior space and other interior regions of an instrument can include, for example, those portions of the instrument (e.g., surfaces, components, or portions thereof) that are not exposed to an external environment, not disposed on an exterior of the instrument, and/or not visible from an external view of the instrument. The internal components of the apparatus can include components that include at least a portion that is internally housed and not exposed to an external environment of the instrument. In some cases, an internal component can be entirely housed within exterior portions of the instrument. In some cases, an internal component can include portions that are housed within an interior of the instrument, but also include portion(s) or surface(s) that are externally facing (e.g., exposed to the external environment).

Distal Seal

Figure 7B:
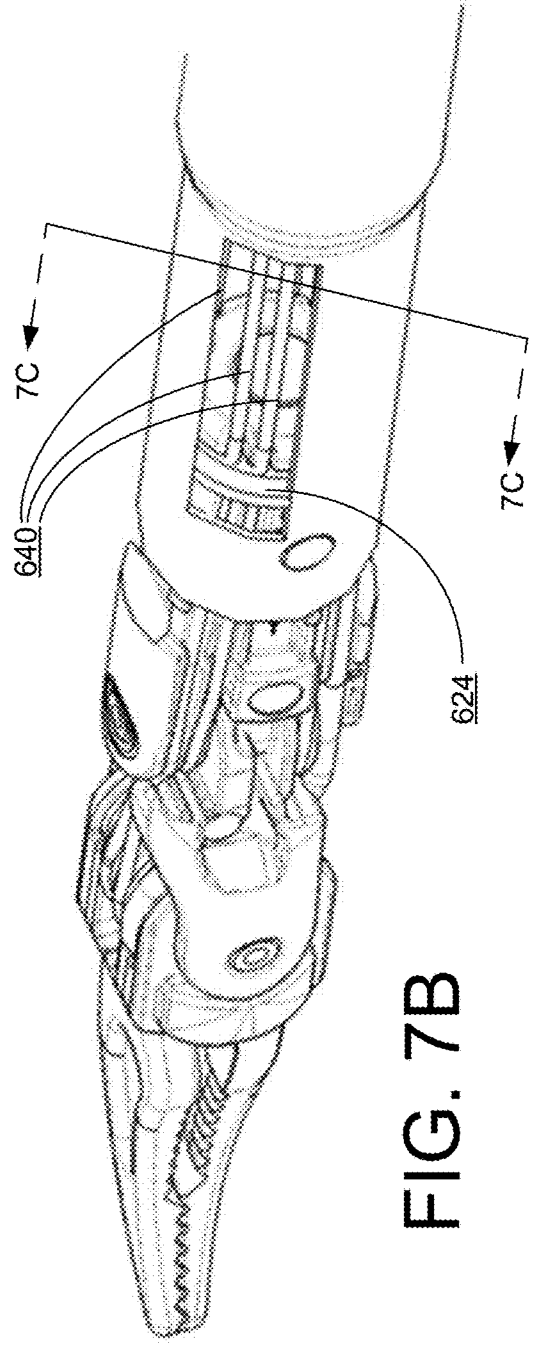
FIG. 7B depicts a perspective view of a distal end of a surgical instrument of a surgical robotic system, according to embodiments.
Figure 7C:
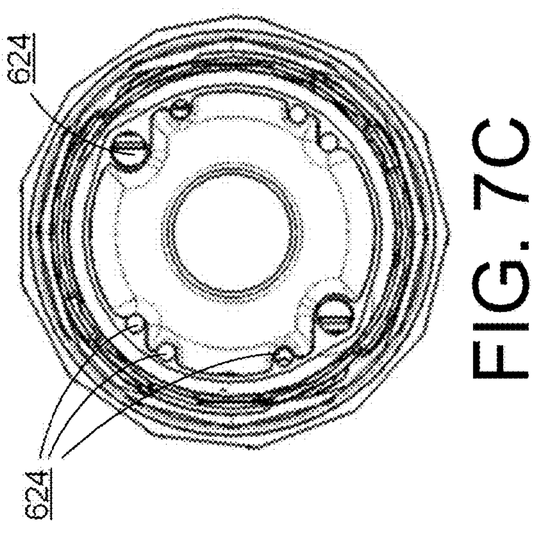
FIG. 7C depicts a cross-sectional view of a distal end of the surgical instrument of FIG. 7B, according to embodiments.

FIG. 7B depicts a perspective view of a distal end of the surgical instrument 600 shown in FIG. 7A. In FIG. 7B, a distal cable seal 624 is disposed inside the shaft 620 adjacent to the end effector 610. The distal cable seal 624 may be configured to reduce fluid ingress into a lumen of the shaft 620. As shown in the cross-sectional view of FIG. 7C, the distal cable seal 624 may define one or more cable openings 624*a*. Each cable openings 624*a* is part of a transmission member path. For example, one or more cables may be configured to translate through a respective cable opening 624*a*. A transmission member path may include cable openings 624*a* on opposite sides of the cable seal 624. As shown in FIG. 7C, the distribution of the cable openings 624*a* may be non-homogeneous or non-equidistant such that an amount of sealing material between adjacent cables may be non-uniform. Accordingly, the ability of distal cable seal 624 to accommodate cable translation and uniform seal compression may be limited. Moreover, the non-homogeneous distribution of the cable openings 624*a* may increase the difficulty of assembly of the transmission members 640 to the cable openings 624*a*. As discussed in more detail below with respect to FIGS. 8A and 8B, failure of a distal seal (or lack of a distal seal) may result in fluid ingress into an instrument 600 that may further result in fluid ingress into an instrument hub 622 and fluid-sensitive electronic components.

Figure 8A:
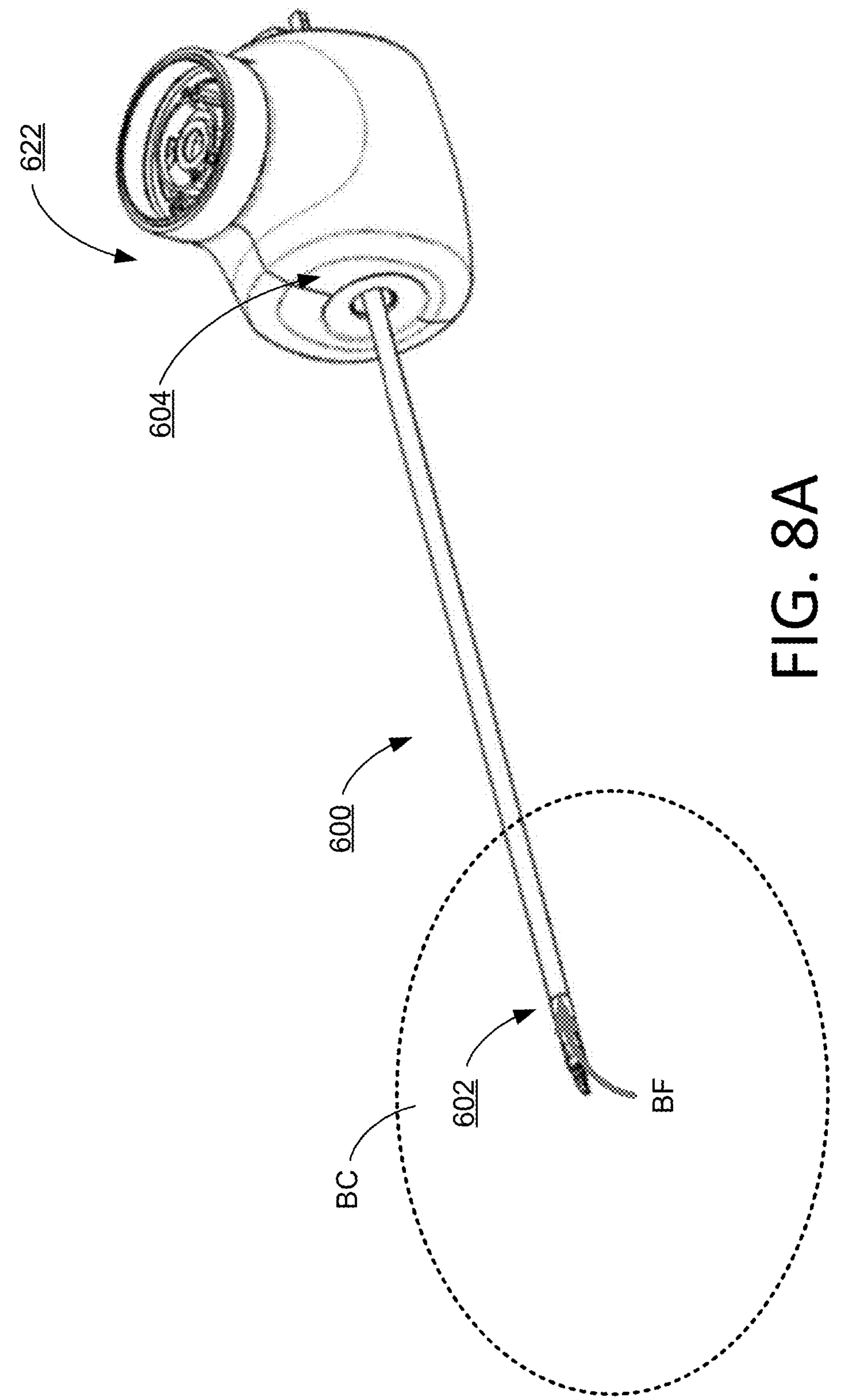
FIG. 8A depicts a perspective view of a surgical instrument coupled to an instrument hub of a surgical robotic system, according to embodiments.
Figure 8B:
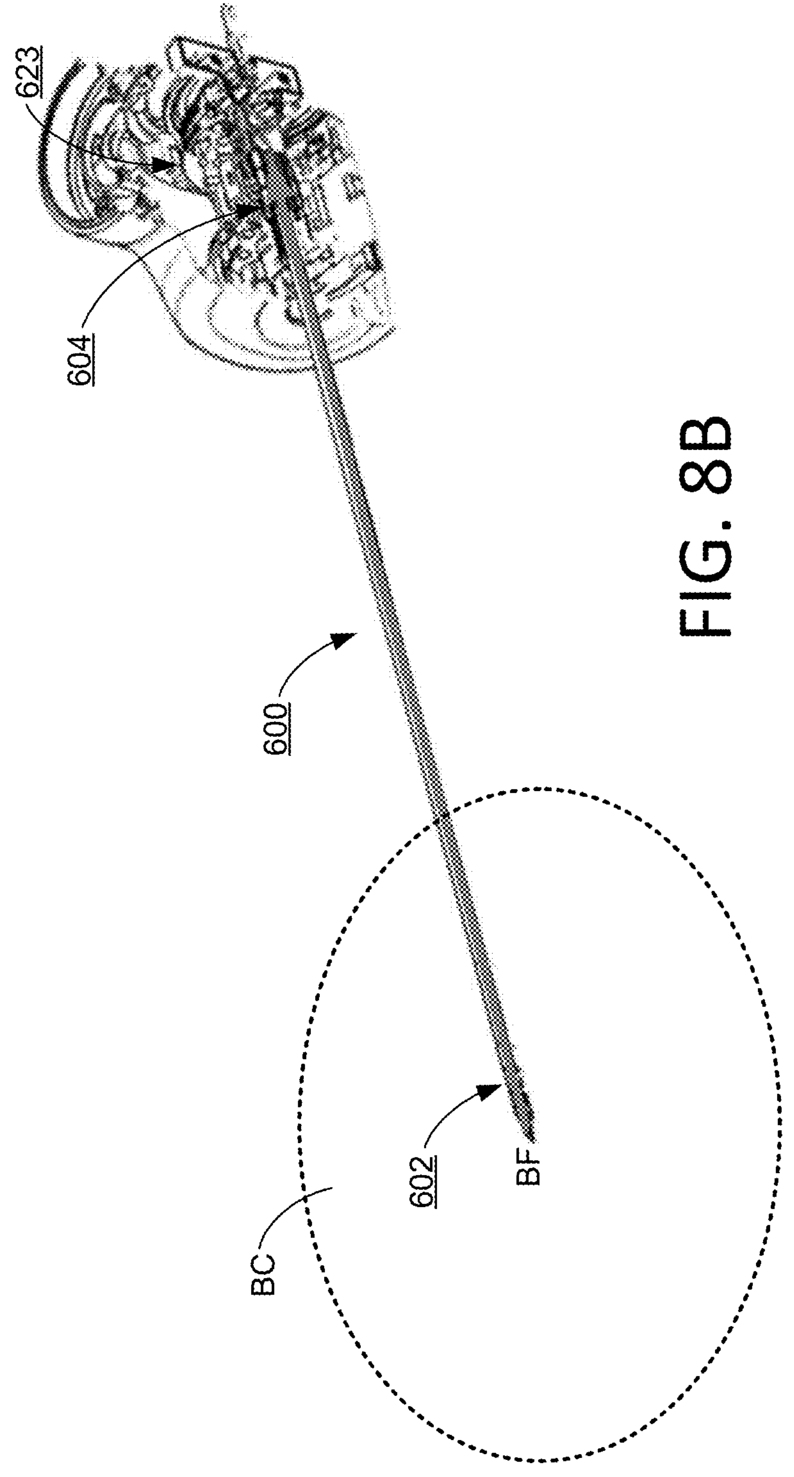
FIG. 8B depicts a cross-sectional view of the surgical instrument coupled to the instrument hub of FIG. 8A, according to embodiments.

FIG. 8A depicts a perspective view of a surgical instrument 600 coupled to an instrument hub 622 of a surgical robotic system. For example, a proximal side 604 of the instrument 600 may be coupled to the instrument hub 622. A distal side 602 of the instrument 600 may be advanced into a body cavity BC (e.g., patient body). For example, an end effector at a distal end of the instrument 600 may be advanced into a body cavity BC and come into contact with one or more bodily fluids BF (e.g., blood, water, saline, tissue). In some embodiments, the bodily fluids BF may flow through a lumen of the instrument towards a proximal side 604 of the instrument 600. For example, FIG. 8B depicts a cross-sectional view of the surgical instrument 600 coupled to the instrument hub 622 of FIG. 8A where the bodily fluids BF flow through the instrument 660 and into contact with electronic elements 623 of the instrument hub 622. As described in more detail with respect to FIGS. 10 and 11, a proximal seal may be disposed within a shaft of an instrument to provide a fluid-tight seal at a proximal portion of the instrument, thereby preventing fluid ingress into one or more of a sterile interface and a hub of the instrument.

Transmission Member

Figures 9A, 9B, 9C:
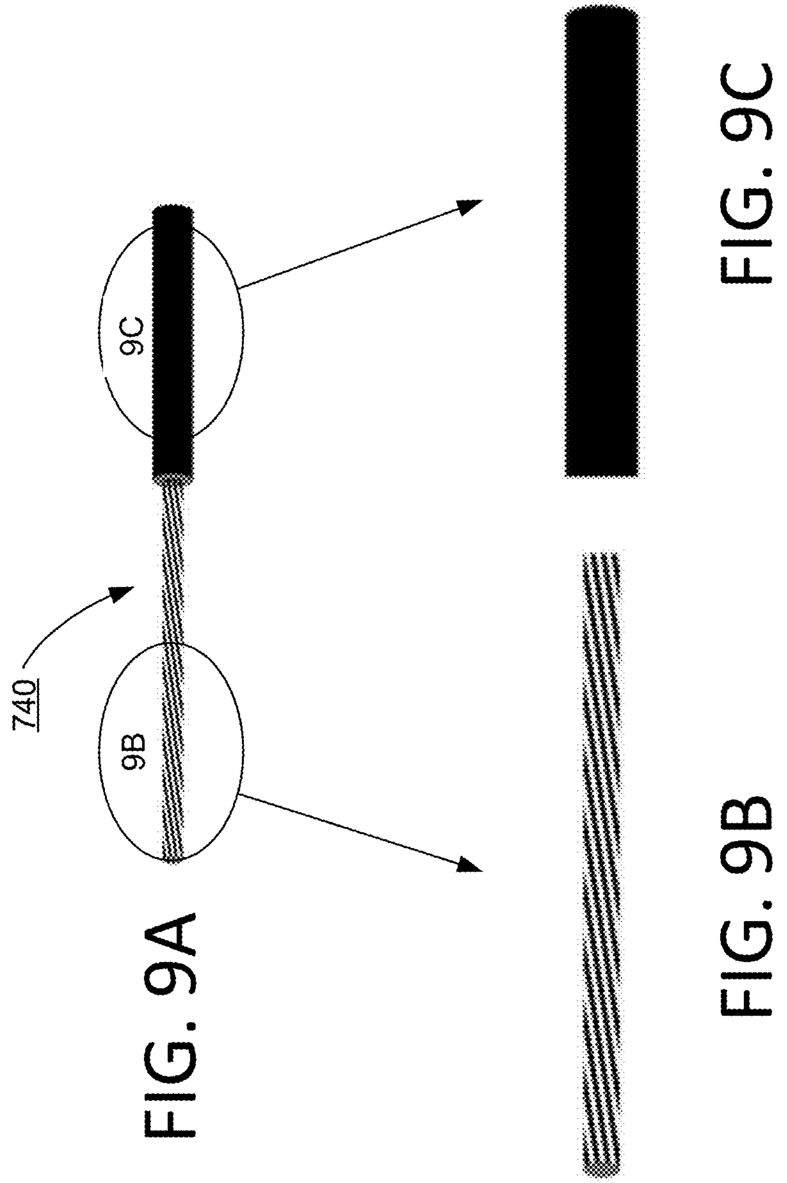
FIG. 9A depicts a side view of a transmission member, according to embodiments.
FIG. 9B depicts a side view of a cable of FIG. 9A, according to embodiments.
FIG. 9C depicts a side view of a hypotube of FIG. 9A, according to embodiments.

FIG. 9A depicts a side view of a transmission member 740. In some embodiments, the transmission member 740 may comprise a cable 742 (FIG. 9B) and a hypotube 744 (FIG. 9C). For example, the cable 742 may be braided (and formed of tungsten) such that a surface texture of the cable 742 may be rough, thereby allowing fluid to flow between the interlaced strands of the cable 742 and consequently facilitating the "pumping effect" of cable translation through a lumen of the instrument. By contrast, the hypotube 744 may comprise a metal such as stainless steel having a substantially smooth surface texture. Due to the differences in surface texture, the translation of the hyoptube 744 may generate less wear relative to translation of the cable 742. For example, the friction between an elastomeric seal and rough cable 742 may be greater than the friction between an elastomeric seal and smooth hypotube 744.

In some embodiments, the cable 742 may be coupled to the hypotube 744. For example, a proximal portion of the cable 742 may be coupled to a distal portion of the hyoptube 744 such that a distal portion of the transmission member 740 may be more flexible than a proximal portion of the transmission member 740.

Proximal Seal

Figures 10A, 10B:
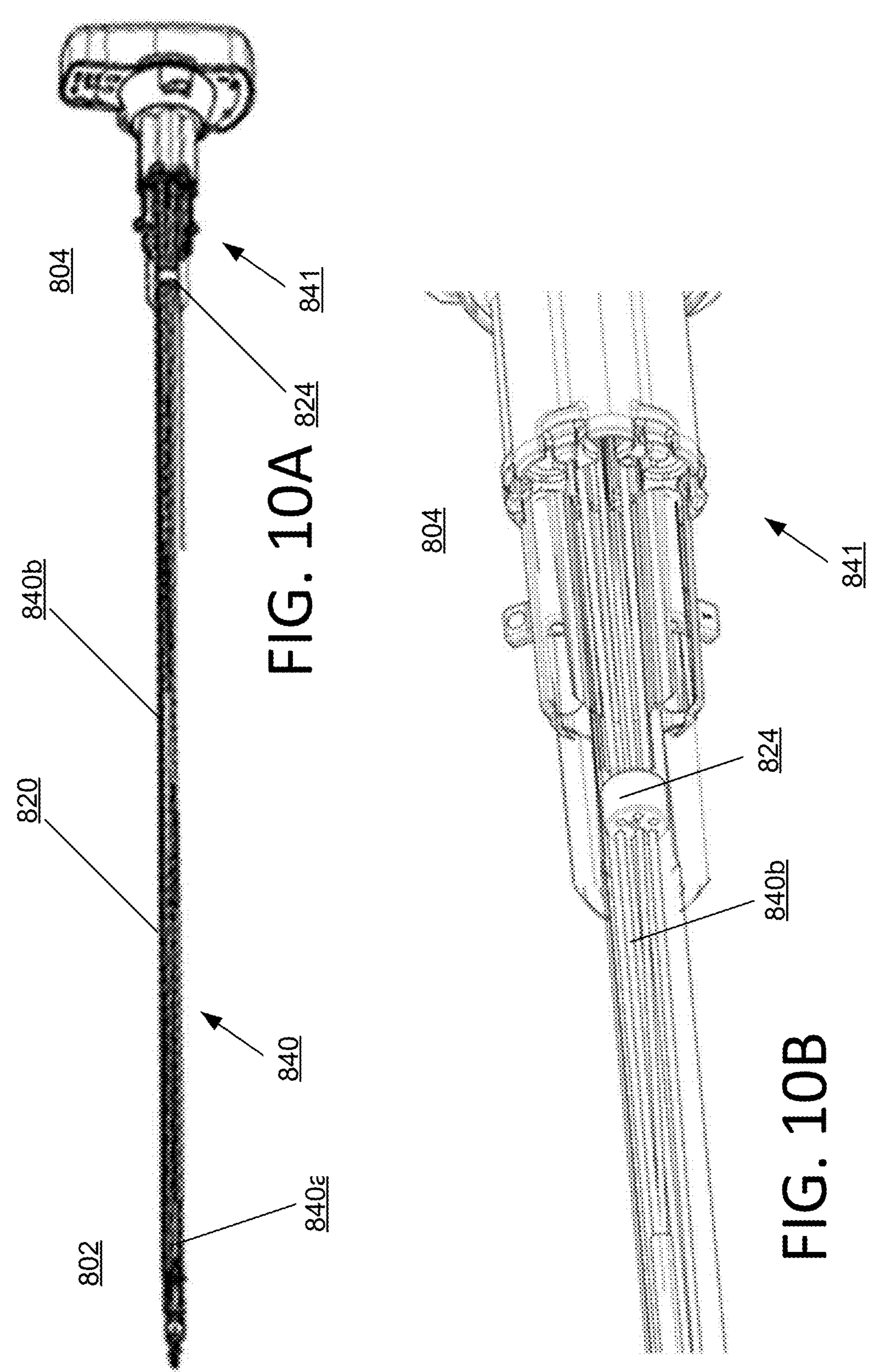
FIG. 10A depicts a cross-sectional side view of a surgical instrument of a surgical robotic system, according to embodiments.
FIG. 10B depicts a detailed cross-sectional side view of a proximal head of the surgical instrument of FIG. 10A, according to embodiments.

Generally, the proximal seals described herein may, for example: provide a fluid-tight seal at a proximal portion of the instrument, thereby preventing fluid ingress into one or more of a sterile interface and a hub of the instrument; improve performance of a seal coupled to one or more transmission members and a shaft of the instrument; reduce the "pumping effect" of transmission cables and corresponding to fluid ingress; provide a seal geometry that improves sealing performance and lifetime; and facilitate assembly of one or more transmission members with a proximal seal of the surgical instrument. For example, FIG. 10A depicts a cross-sectional side view of a surgical instrument 800 of a surgical robotic system including a shaft 820 coupled to a proximal head 841. The shaft 820 may include a proximal end 804 and a distal end 802. The shaft 820 may define a lumen extending between the proximal end 804 and the distal end 802. An end effector 801 may be disposed at the distal end 802 of the shaft 820. A proximal head 841 may be disposed at the proximal end 804 of the shaft 820.

The instrument 800 may include one or more transmission members 840 comprising one or more cables **840*a* and hypotubes 840*b* configured to couple an end effector 801 at a distal end 802 of the instrument 800 and to the proximal head 841 at a proximal end 804 of the instrument 800. In FIG. 10A, the plurality of transmission members 840 may be disposed within the lumen of the shaft 820. For example, each transmission member 840 of the plurality of transmission members may include a distal section comprising a cable 840*a* and a proximal section comprising a hypotube 840*b*. In some embodiments, a distal end of the hypotube 840*b* of each transmission member of the plurality of transmission members may be attached to a proximal end of the cable 840*a* of the transmission member via welding or crimping, e.g., similar to that described with respect to FIGS. 9A-9**C.

Figures 11A, 11B:
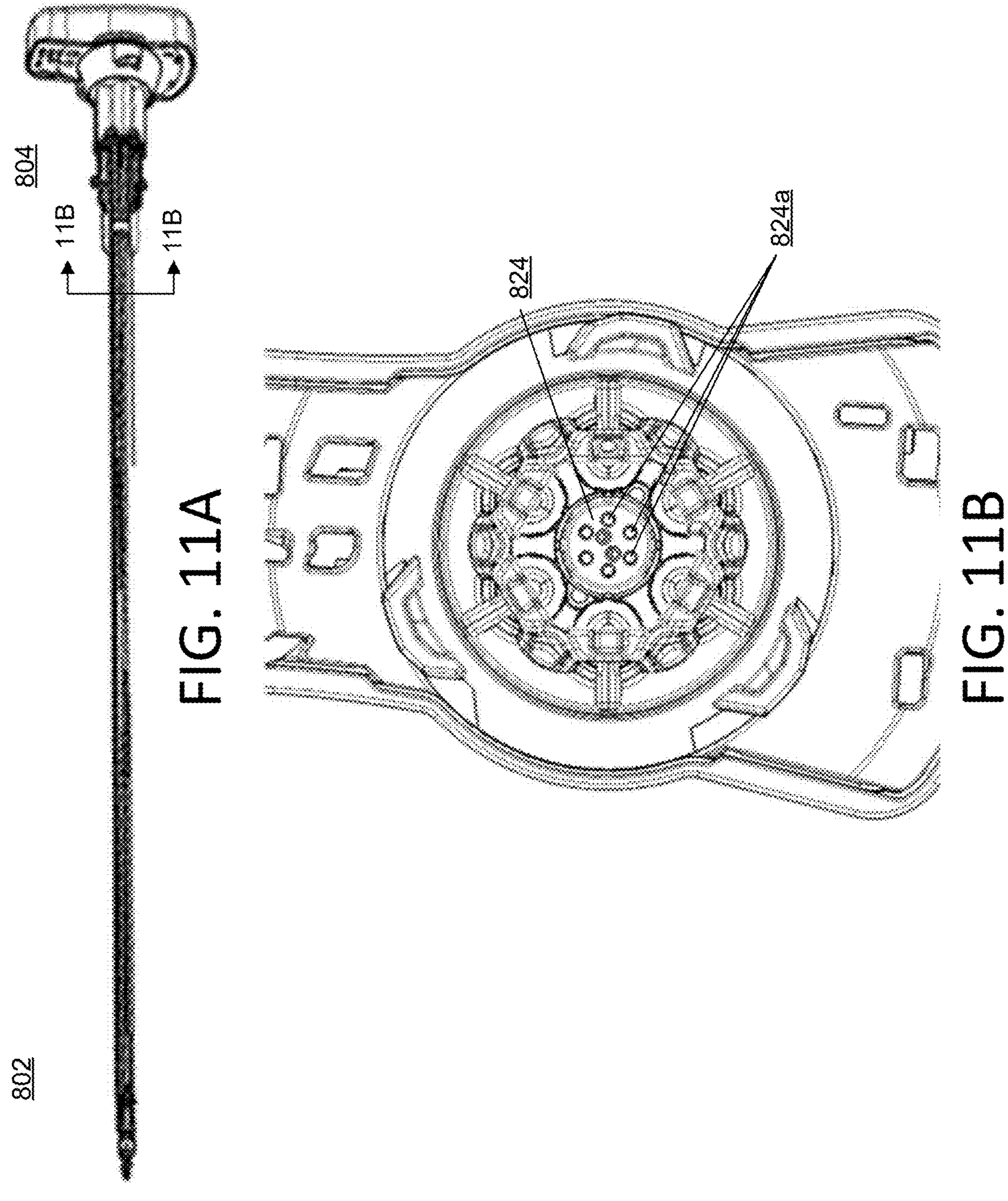
FIG. 11A depicts a cross-sectional side view of a surgical instrument of a surgical robotic system, according to embodiments.
FIG. 11B depicts a detailed cross-sectional side view of a proximal seal of the surgical instrument of FIG. 11A, according to embodiments.

As shown in FIGS. 10B and 11B, a seal 824 (e.g., proximal seal) may be disposed around the plurality of hypotubes **840*b* of transmission members 840 and within the shaft 820 at a proximal end 804 of the shaft 820. For example, the seal 824 may be disposed around the hypotubes 840*b* of the transmission members 840 and configured to seal spaces between outer surfaces of the hypotubes 840*b* and an inner surface of the shaft 820. The plurality of hypotubes 840*b* may be slideable relative to the proximal seal 824. The seal 824 may be configured to form a fluid-tight seal between the plurality of transmission members 840 and an inner surface of the shaft 820, thereby preventing fluid egress from a proximal end of the shaft 820 and fluid ingress into one or more of a sterile interface and a hub of the instrument. That is, fluid that enters and flows through a lumen of the shaft 820 may be prevented from exiting a proximal side 804 of the instrument 800 to prevent, for example, fluid ingress into one or more of a sterile interface and a hub of the instrument. Accordingly, the "pumping effect" of cables may be avoided by coupling the seal 824 to the hypotubes 840*b*, as well as improving sealing performance and lifetime. In some embodiments, the seal 824 may be disposed within a proximal third of the length of the instrument 800**.

The proximal head 841 may be described in more detail with respect to FIGS. 12-15. Generally, the proximal head 841 may further include at least one housing defining a plurality of passages (e.g., slots **934*a*) through which the plurality of engagement elements (e.g., engagement portions 940*a*) extend. For example, each engagement element of the plurality of engagement elements may extend from an interior of the instrument through a passage to an exterior of the instrument. The seal 824 may be disposed distal of the plurality of engagement elements 940. In some embodiments, the proximal head 841 may include a plurality of engagement elements configured to be coupled to one or more drive units of a surgical robotic system that are configured to actuate the plurality of engagement elements. Each transmission member of the plurality of transmission members 840 may couple a separate engagement element of the plurality of engagement elements to the end effector 801 such that the actuation of the plurality of engagement elements causes movement of the end effector 801** in at least one degree-of-freedom.

FIG. 11A depicts a cross-sectional side view of a surgical instrument 800 of a surgical robotic system including a proximal seal 824. FIG. 11B depicts a detailed cross-sectional side view of a proximal seal 824 of the surgical instrument 800. For example, the seal 824 may define a plurality of openings **824*a* through which the plurality of transmission members (e.g., hypotubes 840*b*) extend. The plurality of openings 824*a* may include at least two openings. The plurality of openings 824*a* may be evenly disposed around a periphery of the seal 824 in order to provide a seal geometry that improves sealing performance and lifetime. For example, the distribution of the plurality of openings 824*a* may be symmetrical. For example, the plurality of openings 824*a* may be evenly distributed around a periphery of the seal 824** to provide a seal geometry that improves sealing performance and lifetime, and facilitate assembly of one or more transmission members with a proximal seal of the surgical instrument.

In some embodiments, each transmission member path of the plurality of transmission member paths may include a cable opening **624*a* of the cable seal 624 on a distal side, an opening 824*a* of the proximal seal 824 on a proximal side, and a tubular space between the cable opening 624*a* and the opening 824*a*. The tubular spaces of the plurality of transmission member paths are spaced apart and do not intersect, to prevent the cables from touching each other within the lumen of the shaft 820. Their arrangement is such that they are circumferentially equidistant near the opening 824*a* (see FIG. 11B) and are no longer equidistant near the cable opening 624*a* (see FIG. 7**C). This is because some adjacent cables have to come closer to each other before engaging the mechanism of the instrument's tip.

In some embodiments, the seal 824 is in a compressed state when disposed within the shaft. The openings when the seal is in the compressed state may have a diameter smaller than a diameter of the openings when the seal is in an uncompressed state, which may facilitate assembly of one or more transmission members with a proximal seal of the surgical instrument. For example, the seal 824, when transitioned to the compressed state, may be configured to compress around the plurality of transmission members to form the fluid-tight seal, thereby improving performance of a seal coupled to one or more transmission members and a shaft of the instrument. In some embodiments, the diameter of the seal in the uncompressed state may be between about 5% and about 10% greater than an inner diameter of the shaft, including all ranges and sub-ranges therebetween.

Proximal Head Seal

Figure 12:
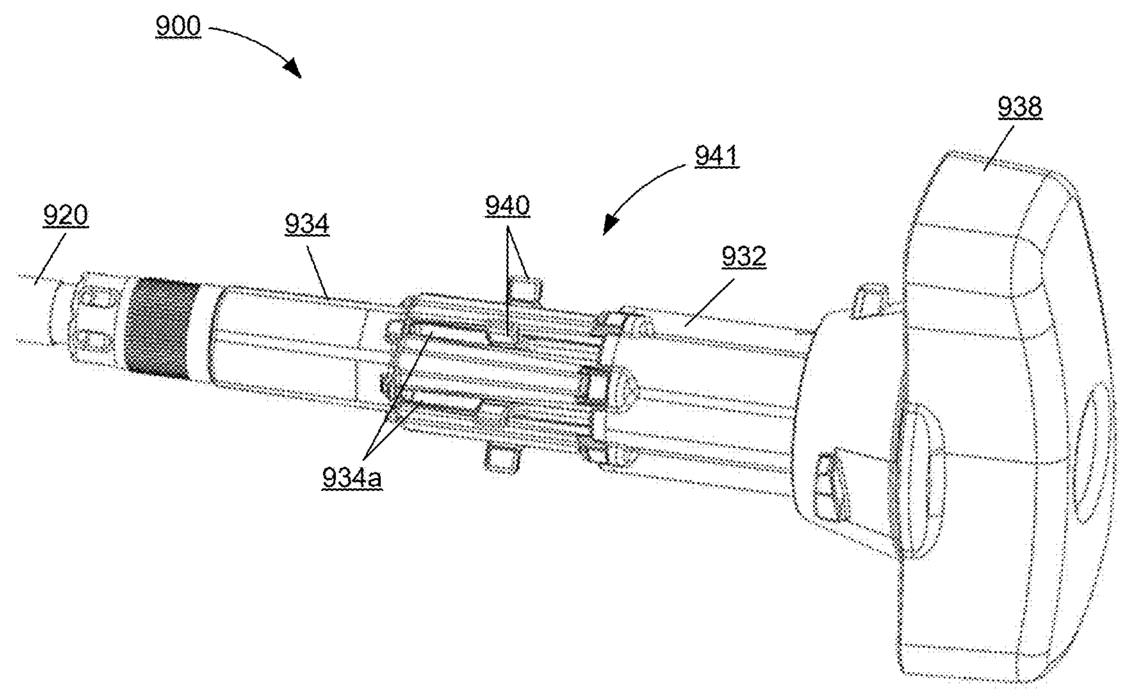
FIG. 12 depicts a perspective view of a proximal end of a surgical instrument of a surgical robotic system, according to embodiments.

Generally, the proximal heads described herein may, for example: provide a fluid-tight seal at a proximal portion of the instrument, thereby preventing fluid ingress into one or more of a sterile interface and a hub of the instrument; facilitate actuation of transmission cables by a driving unit of a surgical robotic system; eliminate a direct path from a lumen of the instrument to an external environment; and retain any liquid within the instrument even when the instrument is angled where the proximal head is lower than the instrument tip. For example, FIG. 12 depicts a perspective view of a proximal end of the instrument 900. The instrument 900 can be functionally and/or structurally similar to other instruments described herein, including the instrument 600, 800, and therefore can include similar components as such instruments. For example, the instrument 900 may include a shaft 920 (e.g., similar to shaft 620, 820) including a proximal end and a distal end. The shaft 920 may define a lumen extending between the proximal end and the distal end. An end effector (e.g., end effector 610, 801) (not shown for the sake of clarity) may be disposed at the distal end of the shaft 920. A proximal head 941 (e.g., proximal head 630) may be disposed at the proximal end of the shaft 920. As shown in FIG. 12, the proximal head 941 may include one or more housings (e.g., proximal housing 932, distal housing 934) defining an internal space or lumen configured to house a plurality of engagement elements 940, and a knob 938 disposed proximal of the housings 932, 934. The knob 938 may comprise a knob body and a knob cover coupled to and proximal to the knob body. The knob 938 may be configured to be rotated and/or translated relative to the proximal head 941 to lock the apparatus to the surgical robotic system. Each engagement element of the plurality of engagement elements 940 may be coupled to the end effector via transmission members 922 (e.g., force transmitting elements, cables) disposed within the lumen.

Figure 13:
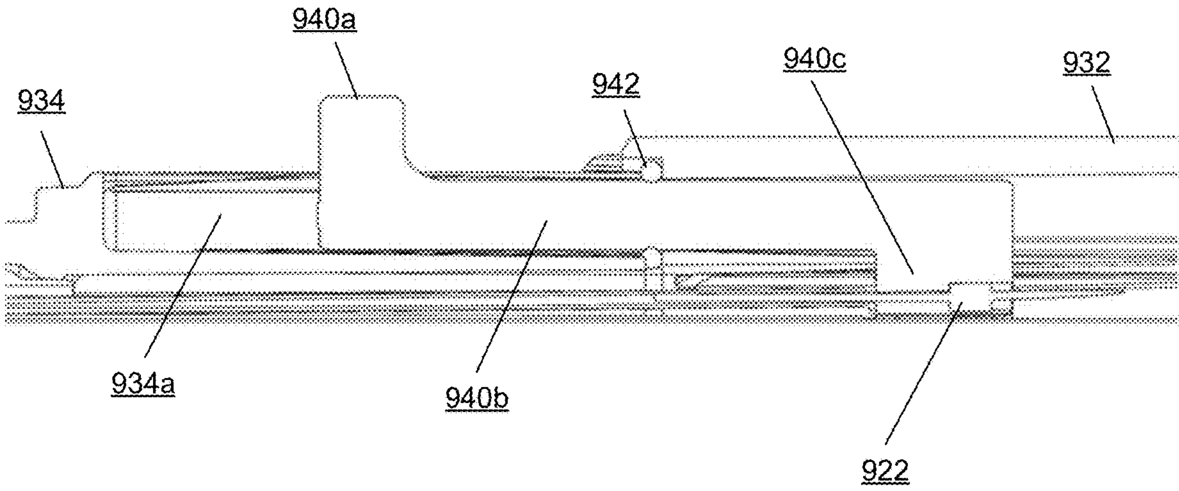
FIG. 13 depicts a close-up, cross-sectional view of a proximal head of the surgical instrument of FIG. 12, according to embodiments.

As shown in the detailed cross-sectional side view of FIG. 13, the proximal and distal housings 932, 934 collectively define a plurality of passages 934*a* within which the plurality of engagement elements 940 translate. For example, the instrument 900 may include a plurality of slots 934*a* disposed circumferentially or peripherally around a longitudinal axis of the instrument 900. The plurality of engagement elements 940 may be disposed in the slots 934*a*, e.g., with each engagement element 940 disposed within a separate slot 934*a* of the plurality of slots. In some embodiments, the proximal head 941 may define a plurality of slots 934*a* and a plurality of engagement elements 940. Each engagement element of the plurality of engagement elements 940 may be disposed in a separate slot of the plurality of slots 934*a*. For example, each engagement element 940 may be configured to longitudinally translate within its respective slot 934*a*. In some embodiments, the plurality of engagement elements 940 may be disposed evenly around a periphery of the distal housing 934. Each engagement element 940 may include a second end 940*a* (e.g., engagement portion) disposed on the exterior of the instrument 900, an elongate portion 940*b*, and a first end 940*c* (e.g., transmission member coupling portion) disposed in the interior of the instrument 900. The engagement portion 940*a* can be configured to engage with one or more receptacles, as described above, to couple the engagement element 940 to one or more drive units of a surgical robotic system. For example, the second end 940*a* may be configured to be coupled to a drive unit of a surgical robotic system (not shown for the sake of clarity) such that actuation of the engagement element 940 by the drive unit is configured to drive movement of the end effector in at least one degree-of-freedom. The first end 940*c* can be configured to couple the engagement element 940 to a proximal end of a transmission member 922 of a plurality of transmission members. The transmission members 922 can then be coupled at their distal end to one or more end effector components, e.g., to drive movement of the end effector, as described above. Each engagement element 940 also includes an elongate portion 940*b* that is configured to fit within the slot and connect the engagement portion 940*a* to the transmission member coupling portion 940*c*. For example, the cylindrical elongate portion 940*b* may be disposed between the first and second ends. The slots 934*a* can be defined by or between the proximal housing 932 and the distal housing 934. In some embodiments, the slots 934*a* can be linear slots or channels, and can define a passageway within which each engagement element 940 can move to translate relative to the proximal housing 932 and the distal housing 934, e.g., to actuate the end effector in at least one degree-of-freedom.

As shown in FIG. 13, a sealing unit 942 may be configured to seal a space between the at least one housing and the plurality of engagement elements to provide a fluid-tight seal at a proximal portion of the instrument, thereby preventing fluid ingress into one or more of a sterile interface and a hub of the instrument 900. The sealing unit 942 can be a unitary structure (e.g., a single component) or include a plurality of seals 942*a*. In some embodiments, the sealing unit 942 may include portions and/or subcomponents that are disposed between the proximal housing 932 and the distal housing 934 and may be configured to seal spaces between each engagement element 940 of the plurality of engagement elements and neighboring portions of the proximal and distal housings. Furthermore, the proximal head 941 may eliminate a direct path from a lumen of the instrument 900 to an external environment such that liquid may be retained within the instrument 900 even when the instrument 900 is angled where the proximal head 941 is lower than the instrument tip.

In some embodiments, the sealing unit 942 (or individual seals of the plurality of seals 942*a* of the sealing unit 942) may be disposed in the slots, e.g., between the proximal housing 932 and the distal housing 934. In some embodiments, each engagement element 940 of the plurality of engagement elements may be configured to be actuated by the drive unit to axially translate the engagement element 940 within the slot 934*a* while the respective seal of the plurality of seals 942*a* disposed around the engagement element 940 in the slot 934*a* is held stationary relative to the engagement element 940 by the proximal and distal housings 932, 934. Accordingly, each engagement element 940 of the plurality of engagement elements may be configured to be actuated by the drive unit to axially translate the engagement element relative to the plurality of seals 942*a*. In some embodiments, each seal of the plurality of seals 942*a* may be disposed on the respective engagement element of the plurality of engagement elements between the first and second ends of the engagement element. In some embodiments, each seal of the plurality of seals 942*a* may include an O-ring that is disposed around the respective engagement element of the plurality of engagement elements. The sealing unit 942 may be configured to form a fluid-tight seal with the plurality of engagement elements 940 to prevent fluids from exiting or leaving an interior space and other interior regions of the instrument 900.

During operation of the instrument, e.g., during surgery, fluids such as bodily fluids may enter an interior space of the instrument 900, e.g., via spaces or openings near a distal end of the instrument 900 (e.g., at or near the end effector). These fluids may travel proximally along the length of the instrument 900 (e.g., along a shaft of the instrument) and reach the proximal head 941 of the instrument 900. If the fluids were allowed to exit from the proximal head 941 of the instrument 900 while the instrument is coupled to the instrument interface of a surgical robotic system, the fluids may reach electronic circuitry or other components of the surgical robotic system and damage those components. To prevent this, the sealing unit 942 can be configured to seal around the engagement elements 940 and between the distal and proximal housings 932, 934 of the instrument to prevent egress of the fluid toward the instrument interface and/or electronic circuitry of the surgical robotic system. As such, the sealing unit 942 permits assembly of the elements of the housing (e.g., the distal and proximal housing 932, 934) in a leak-tight manner. The engagement elements 940 can be configured to extend through the sealing unit 942 (or individual seals of the plurality of seals 942*a* of the sealing unit 942), such that the engagement portions 940*a* of the engagement elements 940 can be engaged with one or more actuators of the robotic system while the transmission member coupling portions 940*c* are coupled to the transmission member 922. The engagement elements 940 can move relative to the sealing unit 942, e.g., in an axial direction. As shown in FIG. 13, the proximal and distal housings 932, 934 include one or more stopping surfaces configured to compress and limit movement of the plurality of seals 942*a* while the plurality of engagement elements 940 axially translates relative to the plurality of seals 942*a*. The engagement elements 940, by being extended through the sealing unit 942, can remain leak-tight while moving in an axial direction.

Figure 14:
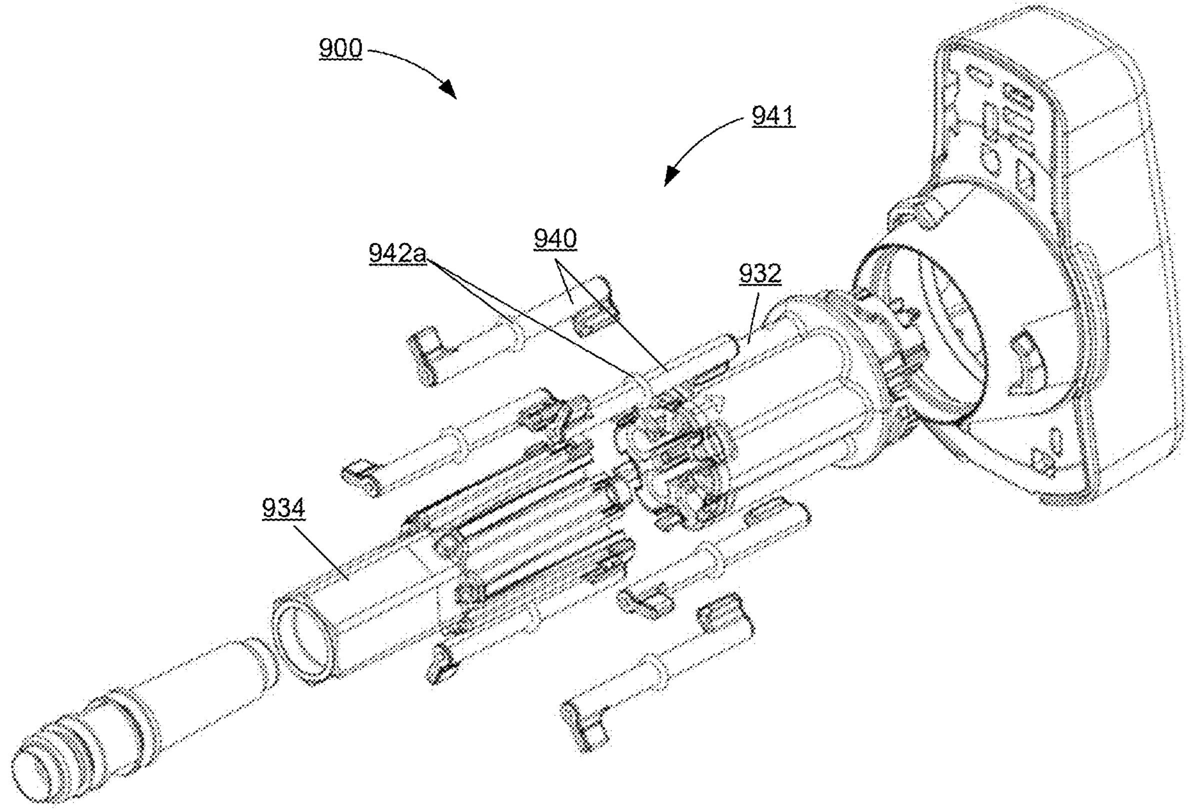
FIG. 14 depicts an exploded perspective view of a proximal head of a surgical instrument of a surgical robotic system, according to embodiments.
Figure 15:
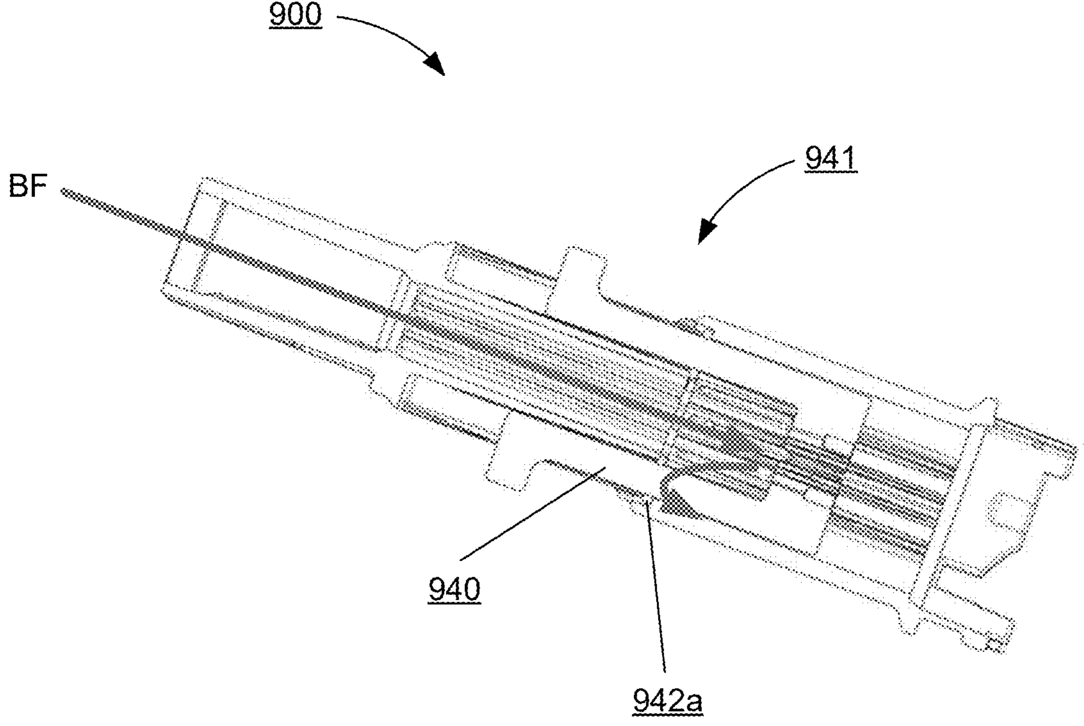
FIG. 15 depicts a cross-sectional view of a proximal head of a surgical instrument, according to embodiments.

FIG. 14 provides a more detailed view of a sealing unit 942 implemented as a plurality of seals 942*a*. As shown in the exploded perspective view of FIG. 14, each seal of the plurality of seals 942*a* may be configured to be disposed around a respective engagement element of the plurality of engagement elements 940 and to seal the spaces between the engagement element and the neighbouring portions of the proximal and distal housings, thereby eliminating a direct path from a lumen of the instrument to an external environment. For example, the cross-sectional view of the proximal head 941 in FIG. 15 depicts how bodily fluids BF within a lumen of the surgical instrument 900 are sealed off from an exterior of the instrument by the seals 942*a* disposed around the respective engagement elements 940. In some embodiments, each seal of the plurality of seals 942*a* may include an O-ring. In some embodiments, each O-ring of the plurality of seals 942*a* may be disposed around the cylindrical elongate portion 940*b* of the respective engagement element of the plurality of engagement elements 940.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, and/or method described herein. In addition, any combination of two or more such features, systems, articles, materials, and/or methods, if such features, systems, articles, materials, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

The indefinite articles "a" and "an," as used herein in the specification and in the claims, unless clearly indicated to the contrary, should be understood to mean "at least one."

As used herein, the phrase "at least one" or "one or more," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one implementation, to at least one, optionally including more than one, A, with no B present (and optionally including elements other than B); in another implementation, to at least one, optionally including more than one, B, with no A present (and optionally including elements other than A); in yet another implementation, to at least one, optionally including more than one, A, and at least one, optionally including more than one, B (and optionally including other elements); etc.

As used herein, the term "and/or" when used to reference to a list of one or more elements includes an element selected from any one or more of the elements in the list of elements, but not necessarily including each and every element specifically listed within the list of elements and not excluding any combinations of elements in the list of elements.

As used herein, the term "unit" can refer to multiple features or a singular feature with one or more parts and/or components.

The invention claimed is:

1. An apparatus, comprising:

a shaft including a proximal end and a distal end, the shaft defining a lumen extending between the proximal end and the distal end;

an end effector disposed at the distal end of the shaft;

a proximal head disposed at the proximal end of the shaft, the proximal head including at least one housing defining a plurality of slots and a plurality of engagement elements, each engagement element of the plurality of engagement elements being disposed in a separate slot of the plurality of slots, each engagement element of the plurality of engagement elements having a first end that is coupled to the end effector via a transmission member and a second end that is configured to be coupled to a drive unit of a surgical robotic system such that actuation of the engagement element by the drive unit is configured to drive movement of the end effector in at least one degree-of-freedom; and a sealing unit including a plurality of seals, the sealing unit configured to seal a space between the at least one housing and the plurality of engagement elements, wherein each seal of the plurality of seals includes an O-ring.

2. The apparatus of claim 1, wherein the at least one housing includes a proximal housing and a distal housing, the proximal and distal housings collectively defining a plurality of passages within which the plurality of engagement elements translate.

3. The apparatus of claim 2, wherein the sealing unit is disposed between the proximal housing and the distal housing and is configured to seal spaces between each engagement element of the plurality of engagement elements and neighboring portions of the proximal and distal housings.

4. The apparatus of claim 3, wherein each seal of the plurality of seals configured to be disposed around a respective engagement element of the plurality of engagement elements and to seal the spaces between the engagement element and the neighboring portions of the proximal and distal housings.

5. The apparatus of claim 4, wherein each engagement element of the plurality of engagement elements is configured to be actuated by the drive unit to axially translate the engagement element while the respective seal of the plurality of seals disposed around the engagement element is held stationary relative to the engagement element by the proximal and distal housings.

6. The apparatus of claim 4, wherein each seal of the plurality of seals is disposed on the respective engagement element of the plurality of engagement elements between the first and second ends of the engagement element.

7. The apparatus of claim 1, wherein each engagement element of the plurality of engagement elements is configured to be actuated by the drive unit to axially translate the engagement element relative to the sealing unit.

8. The apparatus of claim 1, further comprising a knob, the knob configured to be rotated and/or translated relative to the proximal head to lock the apparatus to the surgical robotic system.

9. The apparatus of claim 1, wherein each transmission member includes a distal section comprising a cable and a proximal section comprising a hypotube, the apparatus further comprising:

a seal disposed around the hypotubes of the transmission members and configured to seal spaces between outer surfaces of the hypotubes and an inner surface of the shaft.

10. The apparatus of claim 9, wherein the seal includes a plurality of openings that are distributed around a periphery of the seal.

11. An apparatus, comprising:

a shaft including a proximal end and a distal end, the shaft defining a lumen extending between the proximal end and the distal end;

an end effector disposed at the distal end of the shaft;

a proximal head disposed at the proximal end of the shaft, the proximal head including a plurality of engagement elements, each engagement element of the plurality of engagement elements extending from an interior of the apparatus through a passage to an exterior of the apparatus, each engagement element of the plurality of engagement elements having a first end disposed in the interior that is coupled to the end effector via a transmission member and a second end disposed on the exterior that is configured to be coupled to a drive unit of a surgical robotic system such that actuation of the engagement element by the drive unit is configured to drive movement of the end effector in at least one degree-of-freedom; and a plurality of seals, each seal of the plurality of seals includes an O-ring being disposed around a respective engagement element of the plurality of engagement elements at the passage.

12. The apparatus of claim 11, wherein each engagement element of the plurality of engagement elements includes a cylindrical elongate portion disposed between the first and second ends, each O-ring of the plurality of seals being disposed around the cylindrical elongate portion of the plurality of engagement elements.

13. The apparatus of claim 11, wherein the proximal head further includes a housing that defines a plurality of slots, each engagement element of the plurality of engagement elements being disposed within a separate slot of the plurality of slots and being configured to axially translate within the slot in response to the actuation of the engagement element by the drive unit.

14. The apparatus of claim 13, wherein the plurality of engagement elements is disposed around a periphery of the housing.

15. The apparatus of claim 11, wherein each engagement element of the plurality of engagement elements is configured to be actuated by the drive unit to axially translate the engagement element relative to the plurality of seals.

16. The apparatus of claim 15, wherein the proximal head further includes a proximal housing and a distal housing, the proximal and distal housings collectively defining the passages through which the plurality of engagement elements extend.

17. The apparatus of claim 16, wherein the proximal and distal housings include one or more stopping surfaces configured to limit movement of the plurality of seals while the plurality of engagement elements axially translates relative to the plurality of seals.

18. The apparatus of claim 11, wherein each transmission member includes a distal section comprising a cable and a proximal section comprising a hypotube, the apparatus further comprising:

a seal disposed around the hypotubes of the transmission members and configured to seal spaces between outer surfaces of the hypotubes and an inner surface of the shaft.

19. An apparatus, comprising:

a shaft including a proximal end and a distal end, the shaft defining a lumen extending between the proximal end and the distal end;

an end effector disposed at the distal end of the shaft;

a proximal head disposed at the proximal end of the shaft, the proximal head including at least one housing defining a plurality of slots and a plurality of engagement elements, each engagement element of the plurality of engagement elements being disposed in a separate slot of the plurality of slots, each engagement element of the plurality of engagement elements having a first end that is coupled to the end effector via a transmission member and a second end that is configured to be coupled to a drive unit of a surgical robotic system such that actuation of the engagement element by the drive unit is configured to drive movement of the end effector in at least one degree-of-freedom; and a sealing unit including a plurality of seals, the sealing unit configured to seal a space between the at least one housing and the plurality of engagement elements, wherein each seal of the plurality of seals is disposed on the respective engagement element of the plurality of engagement elements between the first and second ends of the engagement element.

* * * * *